(12) United States Patent
Ooishi

(10) Patent No.: US 9,188,557 B2
(45) Date of Patent: Nov. 17, 2015

(54) CALORIFIC VALUE MEASURING SYSTEM AND CALORIFIC VALUE MEASURING METHOD

(71) Applicant: Azbil Corporation, Tokyo (JP)

(72) Inventor: Yasuharu Ooishi, Tokyo (JP)

(73) Assignee: AZBIL CORPORATION, Tokyo (JP)

( * ) Notice: Subject to any disclaimer, the term of this patent is extended or adjusted under 35 U.S.C. 154(b) by 434 days.

(21) Appl. No.: 13/739,039

(22) Filed: Jan. 11, 2013

(65) Prior Publication Data

US 2013/0259084 A1    Oct. 3, 2013

(30) Foreign Application Priority Data

Mar. 27, 2012   (JP) .................................. 2012-072195

(51) Int. Cl.
   *G01N 25/22*   (2006.01)
   *G01N 25/18*   (2006.01)
   *G01N 33/22*   (2006.01)

(52) U.S. Cl.
   CPC .............. *G01N 25/22* (2013.01); *G01N 25/18* (2013.01); *G01N 33/225* (2013.01)

(58) Field of Classification Search
   USPC ................................................ 374/36, 37, 43
   See application file for complete search history.

(56) References Cited

U.S. PATENT DOCUMENTS

| | | | |
|---|---|---|---|
| 3,777,562 A * | 12/1973 | Clingman, Jr. ................. | 374/37 |
| 4,059,982 A | 11/1977 | Bowman | |
| 4,062,236 A * | 12/1977 | Clingman, Jr. .................. | 374/37 |
| 4,956,793 A | 9/1990 | Bonne et al. | |
| 5,169,450 A | 12/1992 | Opad et al. | |
| 5,224,776 A * | 7/1993 | Clingman et al. .............. | 374/36 |
| 5,756,878 A | 5/1998 | Muto et al. | |
| 5,807,749 A * | 9/1998 | Hornemann .................. | 436/143 |
| 6,019,505 A | 2/2000 | Bonne et al. | |
| 6,517,237 B1 | 2/2003 | Hammond et al. | |

(Continued)

FOREIGN PATENT DOCUMENTS

| | | |
|---|---|---|
| CN | 101421592 A | 4/2009 |
| CN | 101504384 A | 8/2009 |

(Continued)

OTHER PUBLICATIONS

Translation of JP2013205105 (Mar. 27, 2012).*

(Continued)

*Primary Examiner* — Mirellys Jagan
(74) *Attorney, Agent, or Firm* — Troutman Sanders LLP

(57) ABSTRACT

A calorific value measuring system having a container filled with a mixed gas to be measured; a microchip includes a heating element producing heat at a plurality of heat producing temperatures, disposed within the container; a measuring portion measuring a value of an electric signal from the heating element contacting the mixed gas being measured, at each of the plurality of heat producing temperatures; an equation storage device storing a calorific value calculating equation that has, for independent variables, the electric signals from the heating element at the plurality of heat producing temperatures and, as the dependent variable, the calorific value; and a calorific value calculating portion calculating the value of the calorific value of the mixed gas being measured by substituting the measured values for the electric signal from the heating element into the independent variables in the calorific value calculating equation.

18 Claims, 21 Drawing Sheets

(56) References Cited

U.S. PATENT DOCUMENTS

| | | |
|---|---|---|
| 6,997,037 B2 | 2/2006 | Thurston |
| 7,091,509 B2 | 8/2006 | Rahmouni et al. |
| 8,005,293 B2 | 8/2011 | Kowalczyk et al. |
| 2004/0261497 A1 | 12/2004 | Thurston et al. |
| 2005/0034532 A1 | 2/2005 | Wible |
| 2005/0049805 A1 | 3/2005 | Bonne et al. |
| 2009/0193872 A1 | 8/2009 | Tokuda et al. |
| 2009/0277246 A1 | 11/2009 | Ooishi et al. |
| 2010/0294021 A1 | 11/2010 | Makino et al. |
| 2011/0185789 A1 | 8/2011 | Ooshi et al. |
| 2011/0257898 A1 | 10/2011 | Ooishi |

FOREIGN PATENT DOCUMENTS

| | | |
|---|---|---|
| CN | 102200521 | 9/2011 |
| CN | 102253078 | 11/2011 |
| EP | 0348244 A2 | 12/1989 |
| EP | 1947450 A1 | 7/2008 |
| EP | 2009431 A1 | 12/2008 |
| EP | 2345891 A | 7/2011 |
| EP | 2369337 A2 | 9/2011 |
| EP | 2369338 A2 | 9/2011 |
| EP | 2372359 | 10/2011 |
| EP | 2381248 A1 | 10/2011 |
| JP | H3-53149 | 3/1991 |
| JP | H5-141999 A | 6/1993 |
| JP | H8-50109 A | 2/1996 |
| JP | H8-75688 A | 3/1996 |
| JP | H09-96617 A | 4/1997 |
| JP | H11-174010 A | 7/1999 |
| JP | 2002-500357 | 1/2002 |
| JP | 2004-514138 A | 5/2004 |
| JP | 2007-248220 A | 9/2007 |
| JP | 2007-292730 A | 11/2007 |
| JP | 2011-209008 A | 10/2011 |
| WO | 02/40992 A1 | 5/2002 |
| WO | 2007/037209 | 4/2007 |
| WO | 2010/038285 | 4/2010 |

OTHER PUBLICATIONS

Ulbig, Peter, et al. "Determination of the calorific value of natural gas by different methods", Thermochimica Acta, Elsevier Science Publishers, Amsterdam, NL, vol. 382, Jan. 2002, pp. 27-35, XP002639490.

Loubar, et al. "A combustionless determination method for combustion properties of natural gases", Fuel, IPC Science and Technology Press, Guildford, GB, vol. 86, No. 16, Oct. 2007, pp. 2535-2544, XP022293299.

Extended European Search Report, dated May 6, 2013, which issued during the prosecution of European Patent Application No. 08877144.9 (EP2345891).

Extended European Search Report, dated May 6, 2013, which issued during the prosecution of European Patent Application No. 11151331.3 (EP2369337).

Extended European Search Report, dated Apr. 5, 2012, which issued during the prosecution of European Patent Application No. 11159687.0 (EP2369338).

Udina S et al: "A micromachined thermoelectric sensor for natural gas analysis: Thermal model and experimental results", Sensors and Actuators B, Elsevier Sequoia S.A., Lausanne, CH, vol. 134, No. 2, Sep. 25, 2008, pp. 551-558, XP025429938.

File History of U.S. Appl. No. 13/090,602.

File History of U.S. Appl. No. 13/121,765.

File History of U.S. Appl. No. 13/462,132.

Extended European Search Report, dated Sep. 22, 2011, which issued during the prosecution of European Patent Application No. 11163139.6 (EP2381248).

Chinese Office Action dated Jan. 22, 2013, which issued during the prosecution of Chinese Patent Application No. 201110111622.8.

Muto H, et al., Netsudendoritsushiki Bunsekikei ni yoru Toshi Gas Hatsunetsuryo Sokutei (Thermal Conductivity Analyzer for City Gas Calorimeter), Savemation Rev, Feb. 1, 1995, vol. 13, No. 1, pp. 35-39.

Ooishi Y, et al., Tennen Gas no Netsuryo Ryuryo Keisoku no Kanosei ni Tsuite (Calorific flow rate measurement of natural gases), Proceedings of Sensing Forum, 2005, vol. 22, pp. 371-375.

Smola, Alex J. and Scholkopf, Bernhard. "A Tutorial on Support Vector Regression", NeuroCOLT Technical Report NC-TR-98-030. 1998.

Chinese Office Action dated Nov. 4, 2014, which issued during prosecution of Chinese Application No. 201310060562.0, which corresponds to the present application.

N. V. Karlov, "Laser Action on Thermal Diffusion of Gases", 1982 Plenum Publishing Corporation, p. 231-239.

S. C. Saxena, "Transport Properties of Gases and Gaseous Mixtures at High Temperatures", Department 0/ Energy Engineering, University of Illinois at Chicago Circle, Chicago, Illinois 60680, Received Dec. 9, 1970, pp. 168-188, High Temperature Science 3,168-188 (1971).

Japanese Office Action dated Jan. 10, 2014, from Japanese Application No. 2010-097139.

\* cited by examiner

CALORIFIC VALUE MEASURING SYSTEM AND CALORIFIC VALUE MEASURING METHOD

CROSS-REFERENCE TO RELATED APPLICATION

This application claims priority to Japanese Patent Application No. 2012-072195, filed Mar. 27, 2012. The entirety of which is incorporated herein by reference.

FIELD OF TECHNOLOGY

The present invention relates to a calorific value measuring system and calorific value measuring method relating to a gas testing technology.

BACKGROUND

Conventionally, it has been necessary to use costly gas chromatography equipment, or the like, to analyze the compliments of a mixed gas when calculating the amount of heat production of a mixed gas. Additionally, there have been proposals for a method for calculating the amount of heat production from a mixed gas by calculating the ratio of methane ($CH_4$), propane ($C_3H_8$), nitrogen ($N_2$), and carbon dioxide gas ($CO_2$) components included in the mixed gas through measuring the thermal conductivity of the mixed gas and the speed of sound in the mixed gas. (See, for example, Japanese Examined Patent Application Publication 2004-514138 ("JP '138").)

However, the method disclosed in JP '138 requires a costly speed-of-sound sensor to measure the speed of sound, in addition to a sensor for measuring the thermal conductivity. Given this, an object of the present invention is the provision of a calorific value measuring system and calorific value measuring method whereby the calorific value of a gas can be measured easily.

SUMMARY

An example of the present invention provides a calorific value calculating equation generating system having (a) a container for the injection of each of a plurality of mixed gases; (b) a heating element, disposed in a container, for producing heat at a plurality of heat producing temperatures; (c) a measuring portion for measuring a value for an electric signal from a heating element at each of a plurality of heat producing temperatures; and (d) an equation generating portion for generating a calorific value calculating equation, based on values for calorific values for a plurality of mixed gases and measured values for electric signals from a heating element at a plurality of heat producing temperatures, using the electric signals from the heating element at the plurality of heat producing temperatures as independent variables and using the calorific value as the dependent variable.

Moreover, an example of the present invention provides a calorific value calculating equation generating method that includes (a) the preparation of a plurality of mixed gases; (b) the heating elements that are in contact with each of the plurality of mixed gases being caused to produce heat at a plurality of heat producing temperatures; (c) the measurement of a value for an electric signal from a heating element at each of a plurality of heat producing temperatures; and (d) the generation of a calorific value calculating equation, based on values for calorific values for a plurality of mixed gases and measured values for electric signals from a heating element at a plurality of heat producing temperatures, using the electric signals from the heating element at the plurality of heat producing temperatures as independent variables and using the calorific value as the dependent variable.

An example of the present invention provides a calorific value measuring system has (a) a container for the injection of a mixed gas being measured; (b) a heating element, disposed in a container, for producing heat at a plurality of heat producing temperatures; (c) a measuring portion for measuring a value for an electric signal from a heating element that is in contact with the mixed gas being measured at each of a plurality of heat producing temperatures; (d) an equation storage device for storing a calorific value calculating equation that uses electric signals from the heating element at the plurality of heat producing temperatures as independent variables and uses the calorific value as the dependent variable; and (e) a calorific value calculating portion for calculating a value for the calorific value of the mixed gas being measured through substituting measured value of an electric signal from the heating element into an independent variable of the calorific value calculating equation.

Moreover, a form of the present invention provides a calorific value measuring method that includes: (a) the preparation of a mixed gas to be measured; (b) the heating element that is in contact with a mixed being measured being caused to produce heat at a plurality of heat producing temperatures; (c) the measurement of a value for an electric signal from a heating element at each of a plurality of heat producing temperatures; (d) the preparation of a calorific value calculating equation that uses electric signals from the heating element at the plurality of heat producing temperatures as independent variables and uses the calorific value as the dependent variable; and (e) the calculation of a value for the calorific value of the mixed gas being measured through substituting measured value of an electric signal from the heating element into an independent variable of the calorific value calculating equation.

The present invention enables the provision of a calorific value measuring system and a calorific value measuring method able to measure the calorific value of a gas easily and accurately.

DETAILED DESCRIPTION

An example of the present invention is described below. In the descriptions of the drawings below, identical or similar components are indicated by identical or similar codes. Note that the diagrams are schematic. Consequently, specific measurements should be evaluated in light of the descriptions below. Furthermore, even within these drawings there may, of course, be portions having differing dimensional relationships and proportions.

Figure 1:
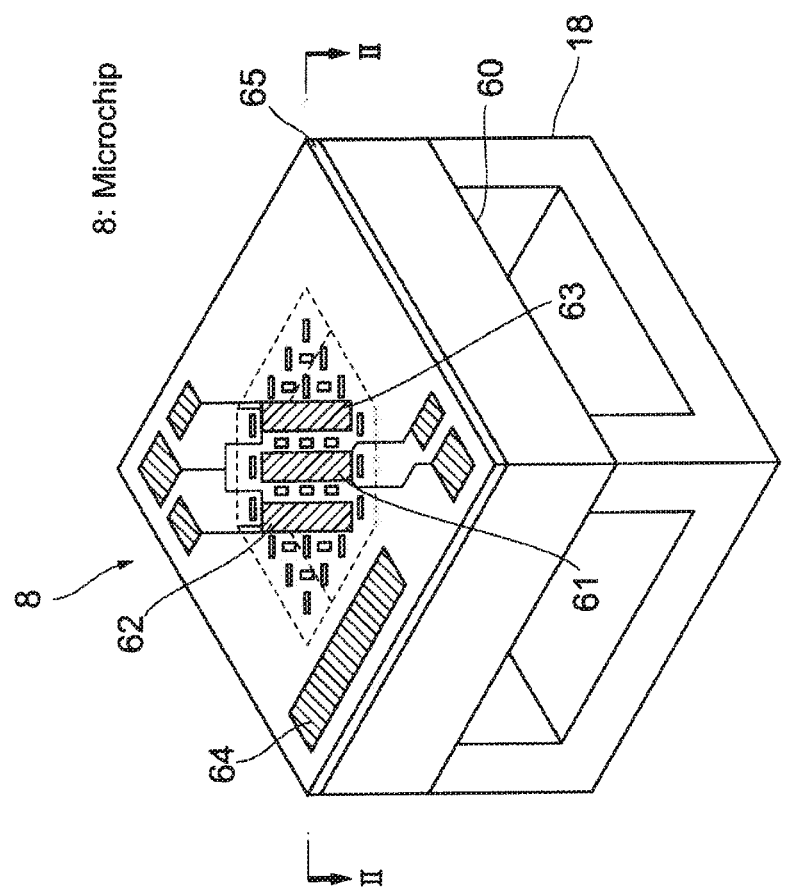
FIG. 1 is a perspective view of a microchip as set forth in an example according to the present invention.
Figure 2:
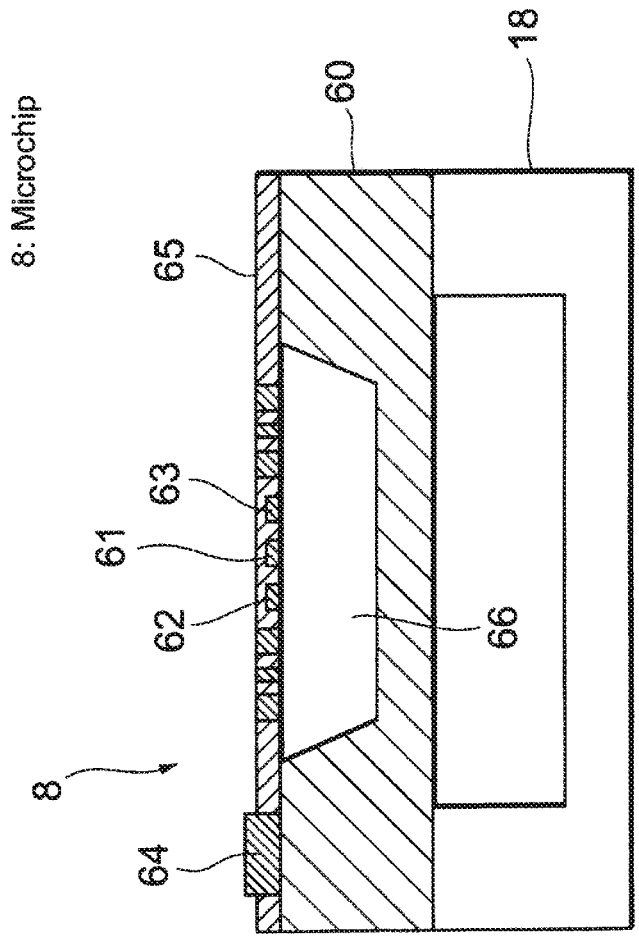
FIG. 2 is a cross-sectional diagram, viewed from the direction of the section II-II in FIG. 1, of the microchip.

First a microchip 8 that is used in a calorific value measuring system as set forth in an example is described in reference to FIG. 1, which is a perspective diagram, and FIG. 2, which is a cross-sectional diagram that is viewed from the direction of the section II-II. The microchip 8 includes a substrate 60, which is provided with a cavity 66, and a insulating layer 65, which is disposed so as to cover the cavity 66 on the substrate 60. The thickness of the substrate 60 is, for example, 0.5 mm. The length and width dimensions of the substrate 60 are, for example, 1.5 mm each. The portion of the insulating film 65 that covers the cavity 66 forms a thermally insulating diaphragm. Moreover, the microchip 8 is provided with a heating element 61 that is provided in the diaphragm part of the insulating film 65, a first temperature measuring element 62 and a second temperature measuring element 63 that are provided at the diaphragm part of the insulating film 65 so as to have the heating element 61 interposed therebetween, and a temperature maintaining element 64 that is provided on the substrate 60.

Figure 3:
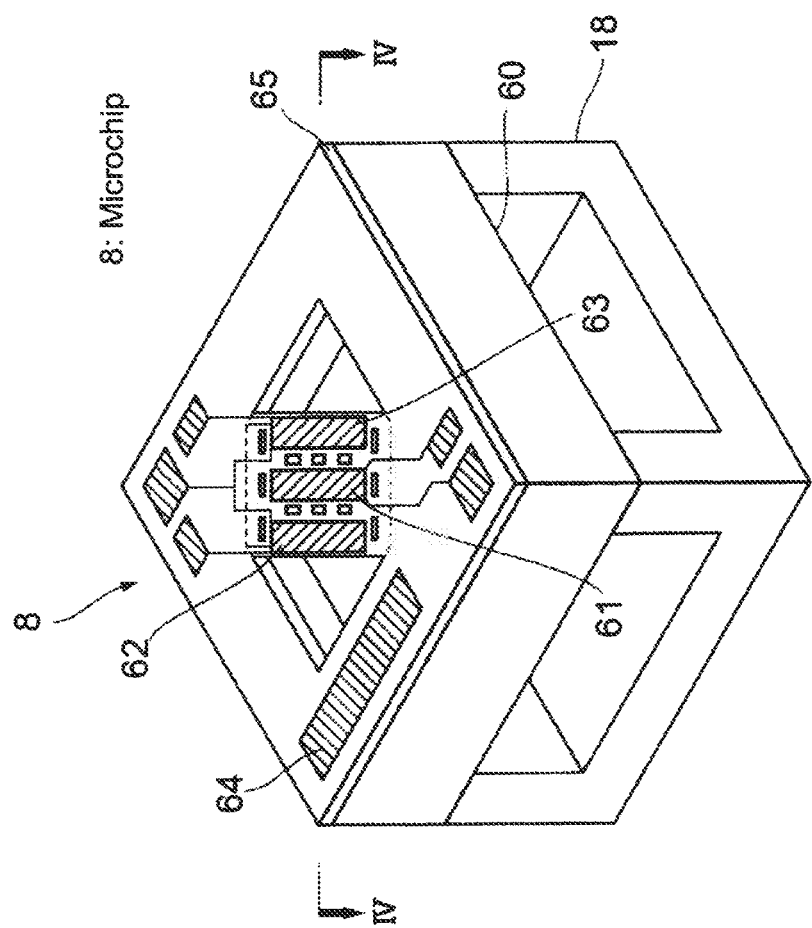
FIG. 3 is a perspective view of another microchip as set forth in another example according to the present invention.
Figure 4:
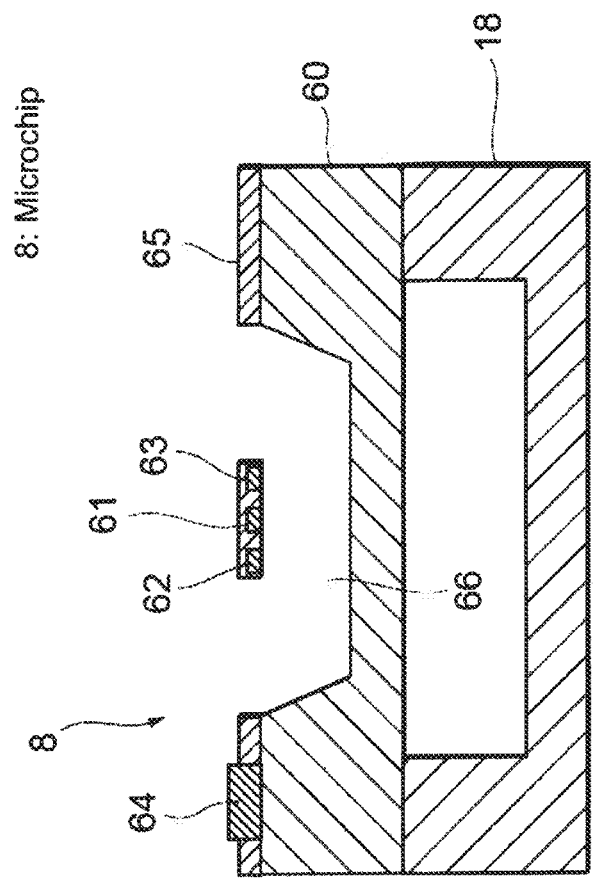
FIG. 4 is a cross-sectional diagram, viewed from the direction of the section IV-IV in FIG. 3, of the other microchip.

A plurality of holes is provided in the diaphragm. The provision of the plurality of holes in the diaphragm expedites the exchange of gases within the cavity 66. Conversely, the insulating layer 65, as illustrated in FIG. 3 and in FIG. 4, which is a cross-sectional diagram when viewed in the direction of the section IV-IV, may be disposed on the substrate 60 so as to cover the cavity 66 in the form of a bridge. This also exposes the inside of the cavity 66, expediting the exchange of gases within the cavity 66.

The heating element 61 is disposed in the center of the portion of the diaphragm of the insulating layer 65 that covers the cavity 66. The heating element 61 is, for example, a resistor, and produces heat through the supply of electric power thereto, to heat the ambient gas that contacts the heating element 61. The first temperature measuring element 62 and the second temperature measuring element 63 are electrical elements that are, for example, passive elements such as resistors, and output electric signals that are dependent on the gas temperatures of the surrounding gases. An example of use of the output signal of the first temperature measuring element 62 is explained below, but there is no limitation thereto, but rather, for example, an average value of the output signal from the first temperature measuring element 62 and the output signal of the second temperature measuring element 63 may be used as the output signal of the temperature measuring elements.

The temperature maintaining element 64 is, for example, a resistor, to which electricity is applied to produce heat, to maintain the substrate 60 at a constant temperature. Silicon (Si), or the like, may be used as the material for the substrate 60. Silicon dioxide ($SiO_2$), or the like, may be used as the material for the insulating film 65. The cavity 66 may be formed through anisotropic etching, or the like. Furthermore, platinum (Pt) or the like may be used as the material for the first temperature measuring element 62, the second temperature measuring element 63, and the temperature maintaining element 64, and they may be formed through a lithographic method, or the like. Moreover, the heating element 61, the first temperature measuring element 62, and the second temperature measuring element 63 may be formed from the same member.

The microchip 8 is secured, for example, to a container, such as a chamber, chamber, or the like, that is filled with the ambient gas, through, for example, a thermally insulating member that is disposed on the bottom face of the microchip 8. Securing the microchip 8 through a thermally insulating member 18 within a container makes the temperature of the microchip 8 less susceptible to temperature variations of the inner wall of the container. The thermal conductivity of the insulating member 18, made from glass, or the like, is, for example, no more than 1.0 W/(m·K).

Figure 5:
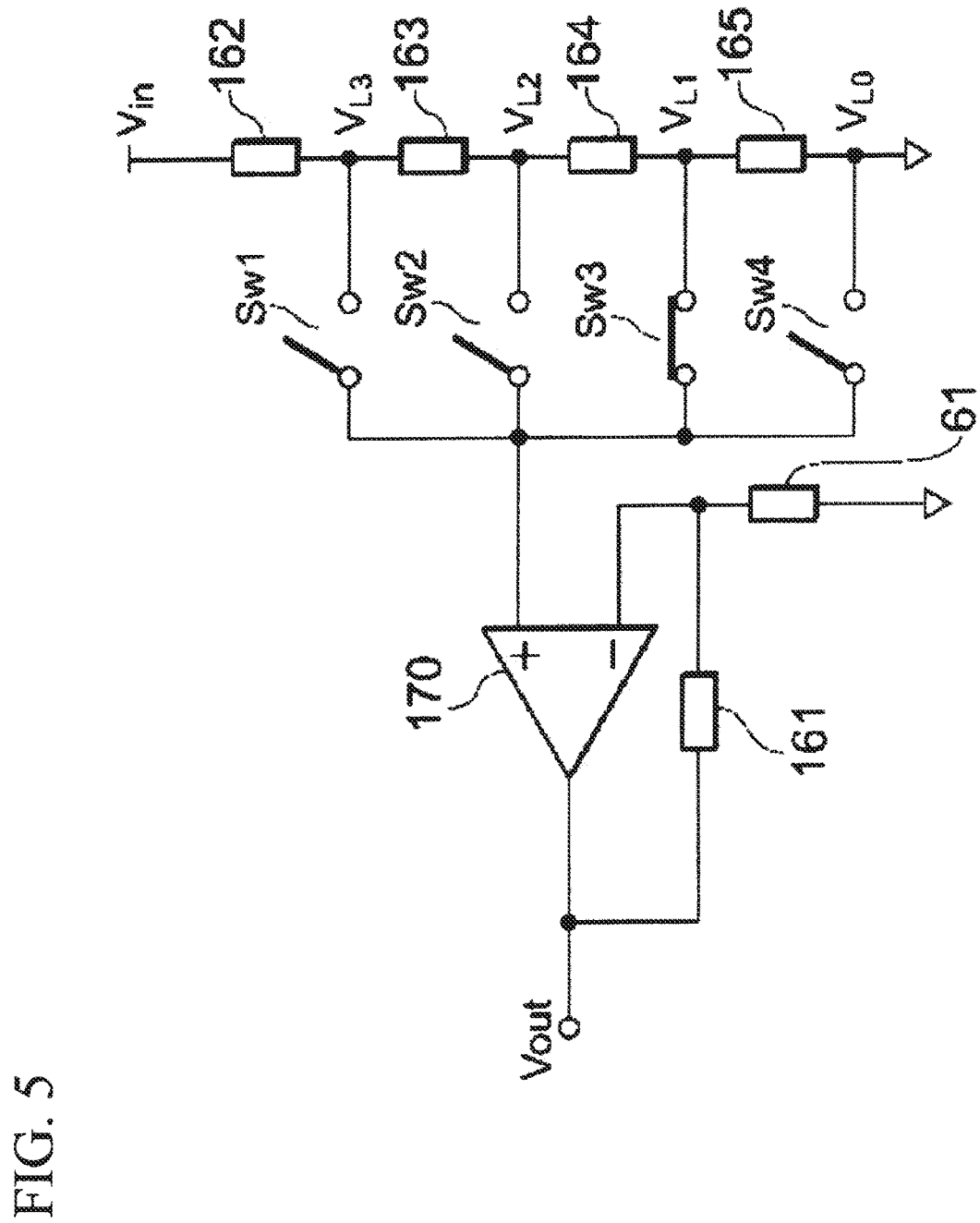
FIG. 5 is a circuit diagram relating to a heating element according to an example of the present invention.

As illustrated in FIG. 5, one end of the heating element 61 is connected electrically to a − input terminal of an operational amplifier 170, for example, with the other end grounded. A resistive element 161 is connected, in parallel, to the − input terminal and the output terminal of the operational amplifier 170. The + input terminal of the operational amplifier 170 is connected electrically between a resistive element 162 and a resistive element 163, which are connected in series, between the resistive element 163 and a resistive element 164, which are connected in series, between the resistive element 164 and a resistive element 165, which are connected in series, or between the resistive element 165 and a ground terminal. Through establishing the resistance values appropriately for each of the resistive elements 162 through 165, a first voltage VL1 can be produced at the part between the resistive element 165 and the resistive element 164, a second voltage VL2 that is higher than the first voltage VL1 will be produced at the part between the resistive element 164 and the resistive element 163, and a third voltage VL3 that is higher than the second voltage VL2 can be produced at the part between the resistive element 163 and the resistive element 162 when, for example, the voltage VIN is applied to one end of the resistive element 162.

A switch SW1 is connected to the connector between the resistive element 162 and the resistive element 163 and the + input terminal of the operational amplifier 170, and a switch SW2 is connected to the connector between the resistive element 163 and the resistive element 164 and the + input terminal of the operational amplifier 170. Furthermore, a switch SW3 is provided between the resistive element 164 and the resistive element 165 and the + input terminal of the operational amplifier 170, and a switch SW4 is provided on the connector between the resistive element 165 and ground terminal and the + input terminal of the operational amplifier 170.

When applying the third voltage $V_{L3}$ to the + input terminal of the operational amplifier 170, only switch SW1 is turned ON, and switches SW2, SW3, and SW4 are turned OFF. When applying the second voltage $V_{L2}$ to the + input terminal of the operational amplifier 170, only switch SW2 is turned ON, and switches SW1, SW3, and SW4 are turned OFF. When applying the first voltage $V_{L1}$ to the + input terminal of the operational amplifier 170, only switch SW3 is turned ON, and switches SW1, SW2, and SW4 are turned OFF. When applying the voltage $V_{L0}$ to the + input terminal of the operational amplifier 170, only switch SW4 is turned ON, and switches SW1, SW2, and SW3 are turned OFF. Consequently, 0V and any of three levels of voltages can be applied to the + input terminal of the operational amplifier 170 through turning the switches SW1, SW2, SW3, and SW4 ON and OFF. Because of this, the applied voltages, which determine the heat producing temperature of the heating element 61, can be set to three different levels through opening and closing the switches SW1, SW2, SW3, and SW4.

Here the temperature of the heating element 61 when the first voltage $V_{L1}$ is applied to the + input terminal of the operational amp defined as $T_{H1}$. Additionally, the temperature of the heating element 61 when the second voltage $V_{L2}$ is applied to the + input terminal of the operational amplifier 170 is defined as $T_{H2}$, and the temperature of the heating element 61 when the third voltage $V_{L3}$ is applied to the + input terminal of the operational amplifier 170 is defined as $T_{H3}$.

Figure 6:
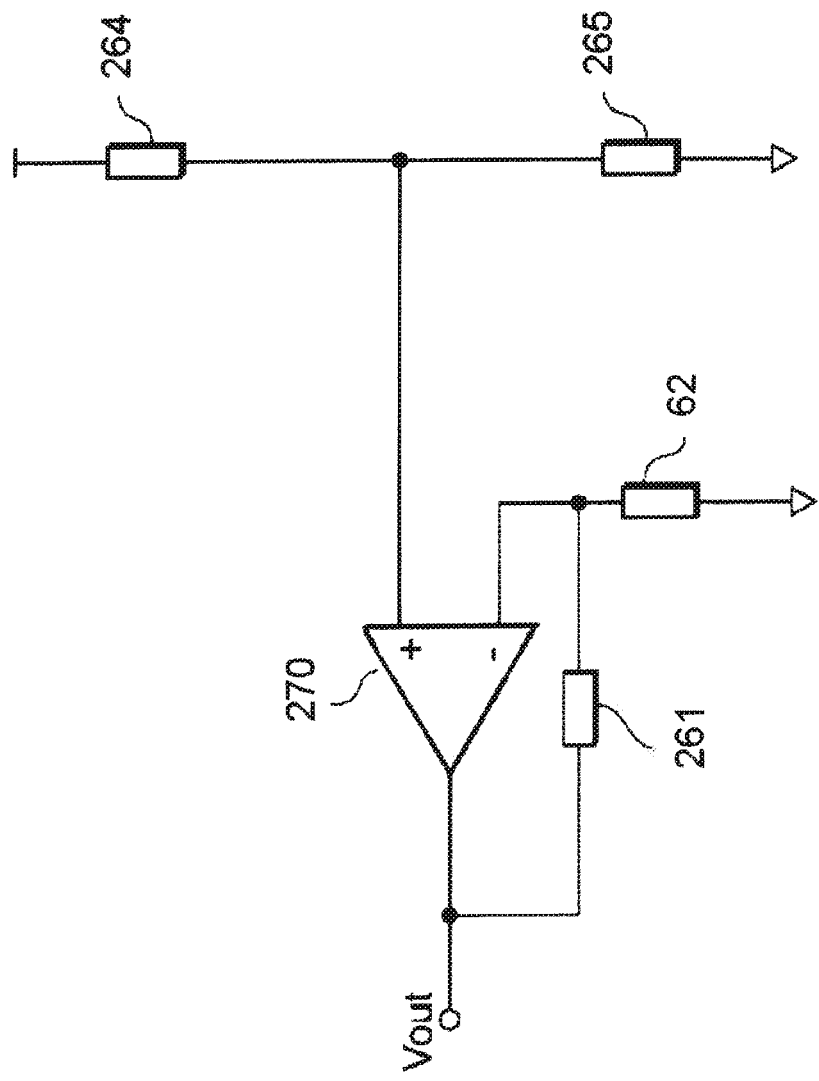
FIG. 6 is a circuit diagram relating to a temperature measuring element according to a further example of the present invention.

As illustrated in FIG. 6, one end of the first temperature measuring element 62 is connected electrically to a − input terminal of an operational amplifier 270, for example, with the other end grounded. A resistive element 261 is connected, in parallel, to the − input terminal and the output terminal of the operational amplifier 270. The + input terminal of the operational amplifier 270 is connected electrically to between a resistive element 264 and a resistive element 265 that are connected in series. This causes a weak voltage of about 0.3 V to be applied to the first temperature measuring element 62.

The resistance value of the heating element 61 illustrated in FIG. 1 and FIG. 2 varies depending on the temperature of the heating element 61. The relationship between the temperature $T_H$ of the heating element 61 and the resistance value $R_H$ of the heating element 61 is given through Equation (1), below:

$$R_H = R_{H\_STD} \times [1 + \alpha_H(T_H - T_{H\_STD}) + \beta_H(T_H - T_{H\_STD})^2] \quad (1)$$

Here $T_{H\_STD}$ indicates a standard temperature for the heating element 61 of, for example, 20° C. $R_{H\_STD}$ indicates the resistance value of the heating element 61 measured in advance at the standards temperature of $T_{H\_STD}$. $\alpha_H$ indicates a first-order resistance temperature coefficient. $\beta_H$ indicates a second-order resistance temperature coefficient.

The resistance value $R_H$ of the heating element 61 is given by Equation (2), below, from the driving power $P_H$ of the heating element 61 and the current $I_H$ that flows through the heating element 61.

$$R_H = P_H/I_H^2 \quad (2)$$

Conversely, the resistance value $R_H$ of the heating element 61 is given by Equation (3), below, from the voltage $V_H$ applied to the heating element 61 and the current $I_H$ that flows through the heating element 61.

$$R_H = V_H/I_H \quad (3)$$

Here the temperature $T_H$ of the heating element 61 reaches a thermal equilibrium and stabilizes between the heating element 61 and the ambient gas. Note that this "thermal equilibrium" refers to a state wherein there is a balance between the heat production by the heating element 61 and the heat dissipation from the heating element 61 into the ambient gas. As shown in Equation (4), below, the driving power $P_H$ of the heating element 61 in the state of thermal equilibrium is divided by the difference $\Delta T_H$ between the temperature $T_H$ of the heating element 61 and the temperature $T_I$ of the ambient gas, to produce the radiation coefficient $M_I$ of the ambient gas. Note that the units for the radiation coefficient $M_I$ are, for example, W/° C.

$$M_I = P_H/(T_H - T_I) \quad (4)$$
$$= P_H/\Delta T_H$$
$$= (V_H^2/R_H)/\Delta T_H$$

From Equation (1), above, the temperature $T_H$ of the heating element 61 is obtained through Equation (5), below:

$$T_H = (1/2\beta_H) \times [-\alpha_H + [\alpha_H^2 - 4\beta_H(1 - R_H/R_{H\_STD})]^{1/2}] + T_{H\_STD} \quad (5)$$

Consequently, the difference $\Delta T_H$ between the temperature $T_H$ of the heating element 61 and the temperature $T_I$ of the ambient gas is given by Equation (6), below:

$$\Delta T_H = (1/2\beta_H) \times [-\alpha_H + [\alpha_H^2 - 4\beta_H(1 - R_H/R_{H\_STD})]^{1/2}] + T_{H\_STD} - T_I \quad (6)$$

The temperature $T_I$ of the ambient gas temperature $T_I$ is approximated by the temperature $T_I$ of the first temperature measuring element 62 when power is applied to the extent that it does not produce heat itself. The relationship between the temperature $T_I$ of the first temperature measuring element 62 and the resistance value $R_I$ of the first temperature measuring element 62 is given by Equation (7), below:

$$R_I = R_{I\_STD} \times [1 + \alpha_I(T_I - T_{I\_STD}) + \beta_I(T_I - T_{I\_STD})^2] \quad (7)$$

Here $T_{I\_STD}$ indicates a standard temperature for the first temperature measuring element 62 of, for example, 20° C. $R_{I\_STD}$ indicates the resistance value of the first temperature measuring element 62, measured in advance at the standard temperature of $T_{I\_STD}$. $\alpha_I$ indicates a first-order resistance temperature coefficient. $\beta_I$ indicates a second-order resistance temperature coefficient. Through Equation (7), above, the temperature $T_I$ of the first temperature measuring element 62 is given by Equation (8), below:

$$T_I = (1/2\beta_I) \times [-\alpha_I + [\alpha_I^2 - 4\beta_I(1 - R_I/R_{I\_STD})]^{1/2}] + T_{I\_STD} \quad (8)$$

Consequently, the radiation coefficient $M_I$ of the ambient gas is given by Equation (9), below.

$$M_I = P_H / \Delta T_H$$

$$= P_H \Big/ \begin{bmatrix} (1/2\beta_H)[-\alpha_H + [\alpha_H^2 - 4\beta_H(1 - R_H/R_{H\_STD})]^{1/2}] + \\ T_{H\_STD} - (1/2\beta_I)[-\alpha_I + [\alpha_I^2 - 4\beta_I(1 - R_I/R_{I\_STD})]^{1/2}] - T_{I\_STD} \end{bmatrix}$$

(9)

The electric current $I_H$ that flows in the heating element 61 and the driving power $P_H$ or the voltage $V_H$ can be measured, and thus the resistance value $R_H$ of the heating element 61 can be calculated from Equation (2) or Equation (3), above. Similarly, it is also possible to calculate the resistance value $R_I$ of the first temperature measuring element 62. Consequently, the radiation coefficient $M_I$ of the ambient gas can be calculated from Equation (9), above, using the microchip 8.

Note that holding the temperature of the substrate 60 constant, using the temperature maintaining element 64, causes the temperature of the ambient gas in the vicinity of the microchip 8, prior to heating by the heating element 61, to approximate the constant temperature of the substrate 60. This suppresses the variation in the temperature of the ambient gas prior to heating by the heating element 61. Further heating, by the heating element 61, the ambient gas for which the temperature variation had been controlled makes it possible to calculate the radiation coefficient $M_I$ with greater accuracy.

Here the ambient gas is a mixed gas, where the mixed gas is assumed to comprise four gas components: gas A, gas B, gas C, and gas D. The total of the volume fraction $V_A$ of the gas A, the volume fraction $V_B$ of the gas B, the volume fraction $V_C$ of the gas C, and the volume fraction $V_D$ of the gas D, as obtained by Equation (10), below, is 1.

$$V_A + V_B + V_C + V_D = 1 \tag{10}$$

Moreover, when the per-unit-volume calorific value of gas A is defined as $K_A$, the per-unit-volume calorific value of gas B is defined as $K_B$, the per-unit-volume calorific value of gas C is defined as $K_C$, and the per-unit-volume calorific value of gas D is defined as $K_D$, then the per-unit-volume calorific value Q of mixed gas is obtained by summing the products of the volume fractions of the individual gas components and the per-unit-volume calorific values of the individual gas components. Consequently, the per-unit-volume calorific value Q of the mixed gas is given by Equation (11), below. Note that the units for the per-unit-volume calorific values are, for example, MJ/m³.

$$Q = K_A \times V_A + K_B \times V_B + K_C \times V_C + K_D \times V_D \tag{11}$$

Moreover, when the per-unit-volume thermal conductivity of gas A is defined as $C_A$, the per-unit-volume thermal conductivity of gas B is defined as $C_B$, the per-unit-volume thermal conductivity of gas C is defined as $C_C$, and the per-unit-volume thermal conductivity of gas D is defined as $C_D$, then the per-unit-volume thermal conductivity $C_I$ of mixed gas is obtained by summing the products of the volume fractions of the individual gas components and the per-unit-volume thermal conductivities of the individual gas components. Consequently, the per-unit-volume thermal conductivity $C_I$ of the mixed gas is given by Equation (12), below. Note that the units for the per-unit-volume thermal conductivities are, for example, W/(mK).

$$C_I = C_A \times V_A + C_B \times V_B + C_C \times V_C + C_D \times V_D \tag{12}$$

Figure 7:
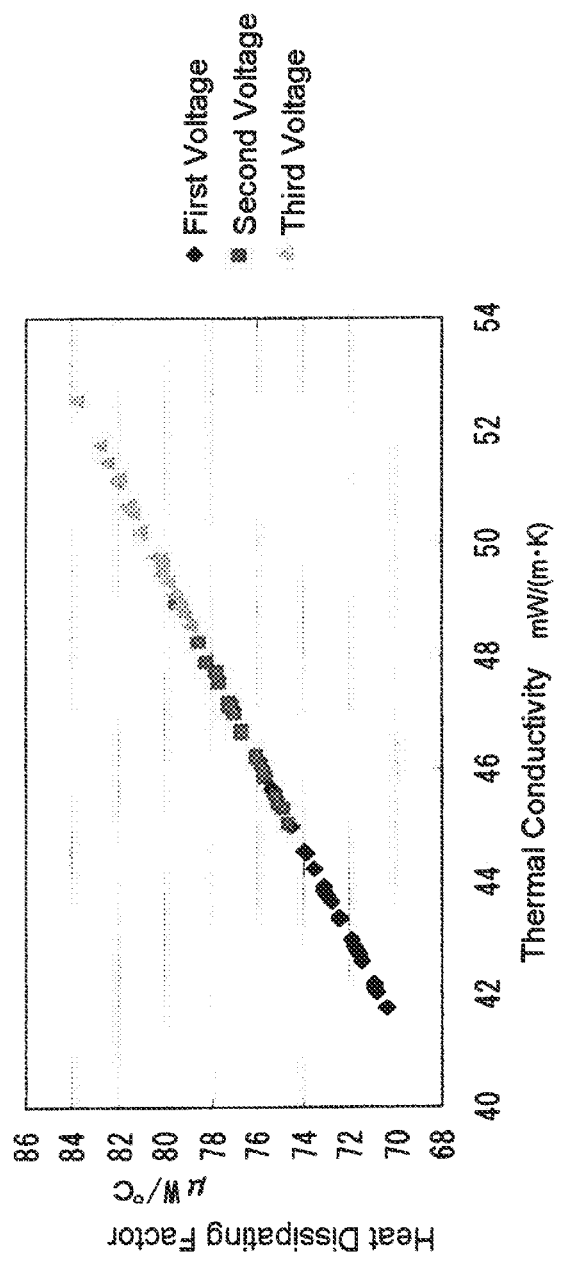
FIG. 7 is a graph illustrating the relationship between the thermal conductivities and the radiation coefficients in an example according to the present invention.

FIG. 7 is a graph of the relationship between the thermal conductivity and the radiation coefficient when a first voltage $V_1$, a second voltage $V_2$ that is larger than the first voltage $V_1$, and a third voltage $V_3$ that is larger than the second voltage $V_2$ are applied to the heating element 61. As illustrated in FIG. 7, typically there is a proportional relationship between the thermal conductivity and the radiation coefficient. Consequently, when the radiation coefficient of gas A is defined as $M_A$, the radiation coefficient of gas B is defined as $M_B$, the radiation coefficient of gas C is defined as $M_C$, and the radiation coefficient of gas D is defined as $M_D$, then the radiation coefficient of the mixed gas $M_I$ is given by summing the products of the volume fractions of the individual gas components and the radiation coefficients of the individual gas components. Consequently, the radiation coefficient $M_I$ of the mixed gas is given by Equation (13), below.

$$M_I = M_A \times V_A + M_B \times V_B + M_C \times V_C + M_D \times V_D \tag{13}$$

Moreover, because the radiation coefficient of the gas is dependent on the temperature $T_H$ of the heating element 61, the radiation coefficient $M_I$ of the mixed gas is given by Equation (14) as a function of the temperature $T_H$ of the heating element 61:

$$M_I(T_H) = M_A(T_H) \times V_A + M_B(T_H) \times V_B + M_C(T_H) \times V_C + M_D(T_H) \times V_D \tag{14}$$

Consequently, when the temperature of the heating element 61 is $T_{H1}$, then the radiation coefficient $M_{I1}(T_{H1})$ of the mixed gas is given by Equation (15), below. Moreover, when the temperature of the heating element 61 is $T_{H2}$, then the radiation coefficient $M_{I2}(T_{H2})$ of the mixed gas is given by Equation (16), below, and when the temperature of the heating element 61 is $T_{H3}$, then the radiation coefficient $M_{I3}(T_{H3})$ of the mixed gas is given by Equation (17), below.

$$M_{I1}(T_{H1}) = M_A(T_{H1}) \times V_A + M_B(T_{H1}) \times V_B + M_C(T_{H1}) \times V_C + M_D(T_{H1}) \times V_D \tag{15}$$

$$M_{I2}(T_{H2}) = M_A(T_{H2}) \times V_A + M_B(T_{H2}) \times V_B + M_C(T_{H2}) \times V_C + M_D(T_{H2}) \times V_D \tag{16}$$

$$M_{I3}(T_{H3}) = M_A(T_{H3}) \times V_A + M_B(T_{H3}) \times V_B + M_C(T_{H3}) \times V_C + M_D(T_{H3}) \times V_D \tag{17}$$

If here the radiation coefficients $M_A(T_H)$, $M_B(T_H)$, $M_C(T_H)$, and $M_D(T_H)$ of the individual gas components are non-linear in respect to the temperature $T_H$ of the heating element 61, then the Equations (15) through (17), above, will have linearly independent relationships. Moreover, even if the radiation coefficients $M_A(T_H)$, $M_B(T_H)$, $M_C(T_H)$, and $M_D(T_H)$ of the individual gas components are linear in respect to the temperature $T_H$ of the heating element 61, if the rates of change of the radiation coefficients $M_A(T_H)$, $M_B(T_H)$, $M_C(T_H)$, and $M_D(T_H)$ of the individual gas components are non-linear in respect to the temperature $T_H$ of the heating element 61 the Equations (15) through (17), above, can have linearly independent relationships. Moreover, if Equations (15) through (17) have a linearly independent relationship, then Equation (10) and Equations (15) through (17) can have a linearly independent relationship.

Figure 8:
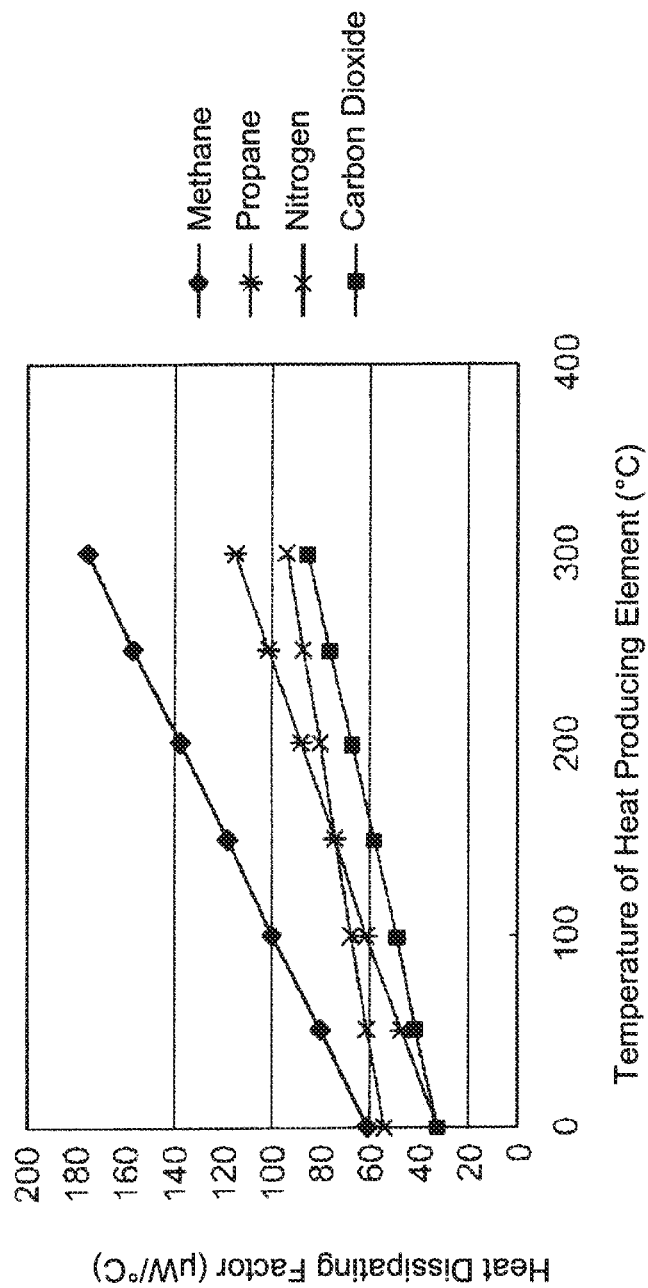
FIG. 8 is a graph illustrating the relationship between the temperature of the heating element and the radiation coefficient of the gas in an example according to the present invention.

FIG. 8 is a graph showing the relationships of the radiation coefficients of methane ($CH_4$), propane ($C_3H_8$), nitrogen ($N_2$), and carbon dioxide ($CO_2$), which are included in natural gas, to the temperature of the heating element 61 which is a heat producing resistance. The radiation coefficients of each of these components (methane ($CH_4$), propane ($C_3H_8$), nitrogen ($N_2$), and carbon dioxide ($CO_2$)) are linear in respect to the temperature of the heating element 61. However, the respective rates of change of the radiation coefficients in respect to the temperature of the heating element 61 are different for methane ($CH_4$), propane ($C_3H_8$), nitrogen ($N_2$), and carbon dioxide ($CO_2$). Consequently, Equations (15) through (17), above, will be linearly independent if the gas components that comprise the mixed gas are methane ($CH_4$), propane ($C_3H_8$), nitrogen ($N_2$), and carbon dioxide ($CO_2$).

The values for the radiation coefficients $M_A(T_{H1})$, $M_B(T_{H1})$, $M_C(T_{H1})$, $M_D(T_{H1})$, $M_A(T_{H2})$, $M_B(T_{H2})$, $M_C(T_{H2})$, $M_D(T_{H2})$, $M_A(T_{H3})$, $M_B(T_{H3})$, $M_C(T_{H3})$, $M_D(T_{H3})$ for the individual gas components in Equation (15) through Equation (17) can be obtained in advance through measurements, or the like. Consequently, when the system of simultaneous equations of Equation (10) and Equation (15) through Equation (17) is solved, the volumetric fraction $V_A$ of the gas A, the volumetric fraction $V_B$ of the gas B, the volumetric fraction $V_C$ of the gas C, and the volumetric fraction $V_D$ of the gas D, respectively, are obtained as functions of the radiation coefficients $M_{I1}(T_{H1})$, $M_{I2}(T_{H2})$, and $M_{I3}(T_{H3})$ of the mixed gas, as shown in equations (18) through (21), below. Note that in Equations (18) through (21), below, $f_n$, where n is a non-negative integer, is a code representing a function:

$$V_A = f_1[M_{I1}(T_{H1}), M_{I2}(T_{H2}), M_{I3}(T_{H3})] \quad (18)$$

$$V_B = f_1[M_{I2}(T_{H1}), M_{I2}(T_{H2}), M_{I3}(T_{H3})] \quad (19)$$

$$V_C = f_3[M_{I1}(T_{H1}), M_{I2}(T_{H2}), M_{I3}(T_{H3})] \quad (20)$$

$$V_D = f_4[M_{I1}(T_{H1}), M_{I2}(T_{H2}), M_{I3}(T_{H3})] \quad (21)$$

Here Equation (22), below, is obtained through substituting Equation (18) through (21) into Equation (11), above.

$$\begin{aligned} Q &= K_A \times V_A + K_B \times V_B + K_C \times V_C + K_D \times V_D \\ &= K_A \times f_1[M_{I1}(T_{H1}), M_{I2}(T_{H2}), M_{I3}(T_{H3})] + \\ &\quad K_B \times f_2[M_{I1}(T_{H1}), M_{I2}(T_{H2}), M_{I3}(T_{H3})] + \\ &\quad K_C \times f_3[M_{I1}(T_{H1}), M_{I2}(T_{H2}), M_{I3}(T_{H3})] + \\ &\quad K_D \times f_4[M_{I1}(T_{H1}), M_{I2}(T_{H2}), M_{I3}(T_{H3})] \end{aligned} \quad (22)$$

As shown in Equation (22), above, the per-unit-volume calorific value Q is obtained as an equation which has, as variables, the radiation coefficients $M_{I1}(T_{H1})$, $M_{I2}(T_{H2})$, and $M_{I3}(T_{H3})$ of the mixed gas when the temperatures of the heating element 61 are $T_{H1}$, $T_{H2}$, and $T_{H3}$. Consequently, the calorific value Q of the mixed gas is given by Equation (23), below, where $g_1$ is a code representing a function.

$$Q = g_1[M_{I1}(T_{H1}), M_{I2}(T_{H2}), M_{I3}(T_{H3})] \quad (23)$$

Consequently, the inventors discovered that, for a mixed gas comprising a gas A, a gas D, a gas C, and a gas D, wherein the volume fraction $V_A$ of the gas A, the volume fraction $V_B$ of the gas B, the volume fraction $V_C$ of the gas C, and the volume fraction $V_D$ of the gas D, are unknown, it is possible to calculate easily the per-unit-volume calorific value of the mixed gas to be measured if Equation (23) is obtained in advance. Specifically, it is possible to use Equation (9), above, to calculate uniquely the calorific value Q of the mixed gas to be measured, through measuring the radiation coefficients $M_{I1}(T_{H1})$, $M_{I2}(T_{H2})$, and $M_{I3}(T_{H3})$ for the mixed gas to be measured, at the heat producing temperatures of $T_{H1}$, $T_{H2}$, and $T_{H3}$ of the heating element 61 and then substituting, into Equation (23).

In the method described above, the calorific value Q is measured through measuring the radiation coefficients $M_{I1}(T_{H1})$, $M_{I2}(T_{H2})$, and $M_{I3}(T_{H3})$ for the mixed gas being measured, using the heating element 61 and the first temperature measuring element 62 of the microchip 8. In contrast, in the method described below, the calorific value Q of the mixed gas can be measured using the heating element 61 alone, without using the first temperature measuring element 62 of the microchip 8.

Figure 9:
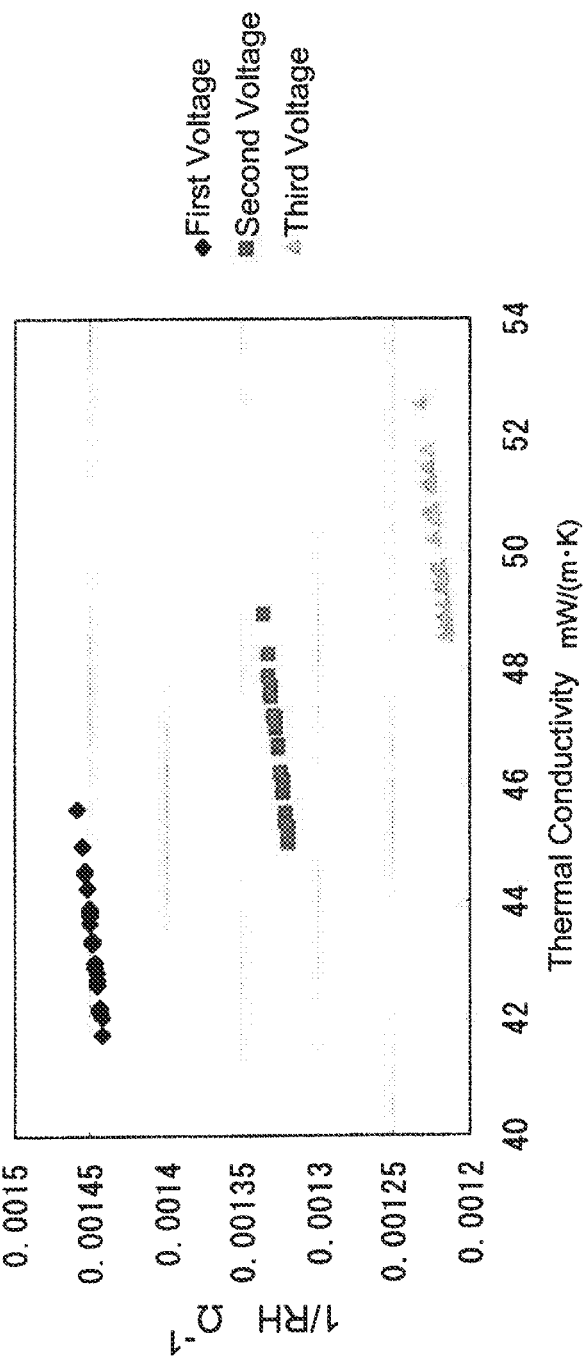
FIG. 9 is a first graph illustrating the relationship between the thermal conductivities and the resistances of the heating elements in an example according to the present invention.
Figure 10:
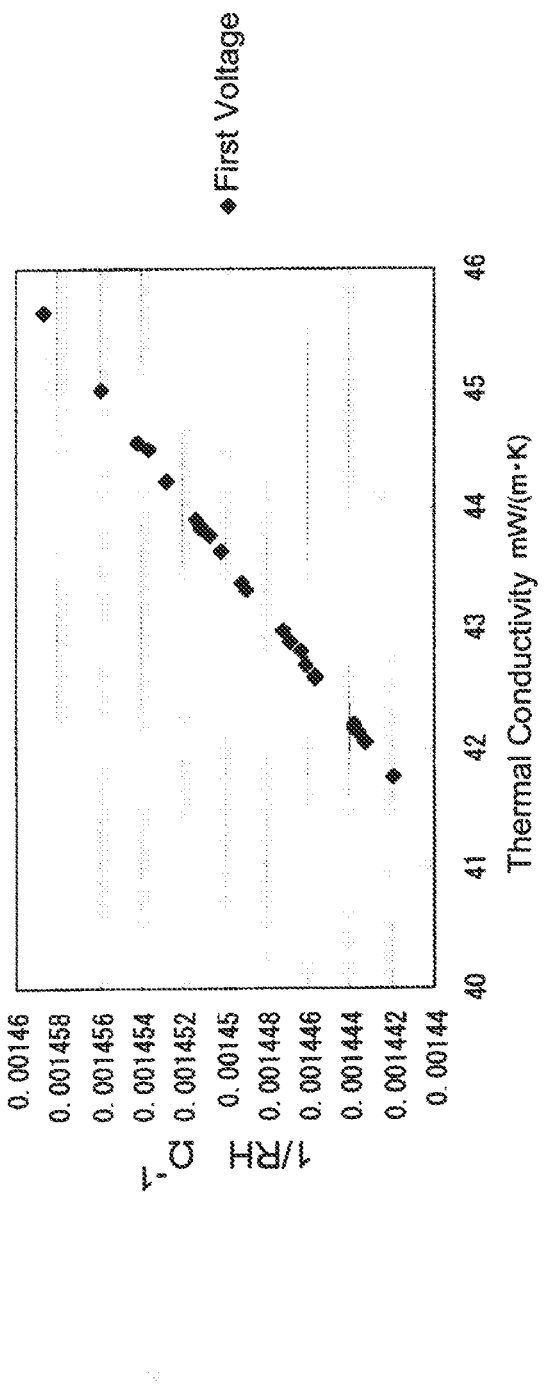
FIG. 10 is a second graph illustrating the relationship between the thermal conductivities and the resistances of the heating elements in another example according to the present invention.
Figure 11:
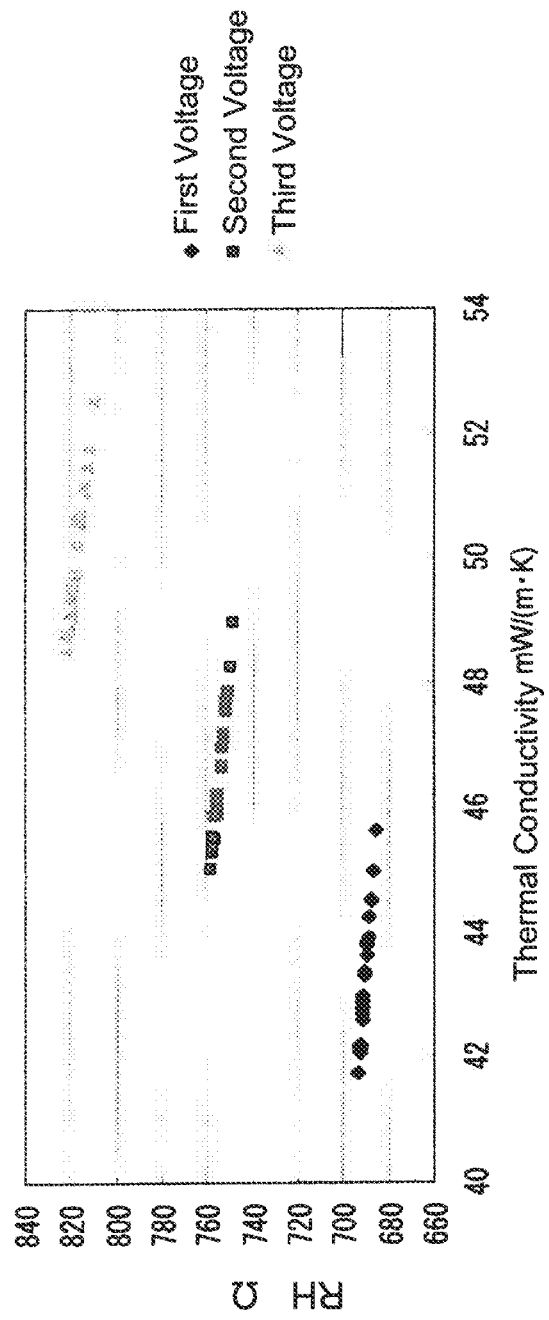
FIG. 11 is a third graph illustrating the relationship between the thermal conductivities and the resistances of the heating elements in a further example according to the present invention.
Figure 12:
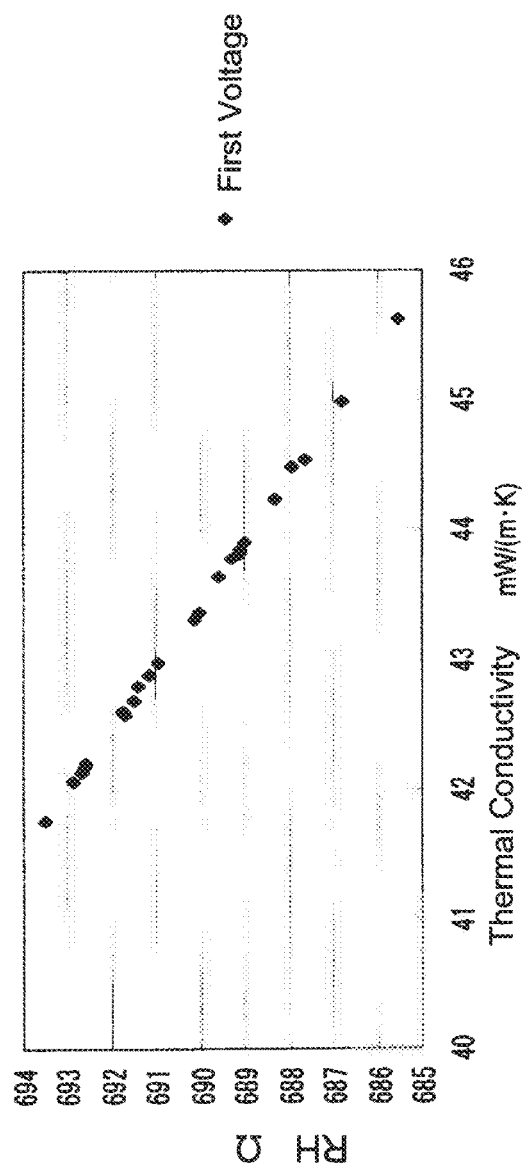
FIG. 12 is a fourth graph illustrating the relationship between the thermal conductivities and the resistances of the heating elements in embodiment yet further example according to the present invention.
Figure 13:
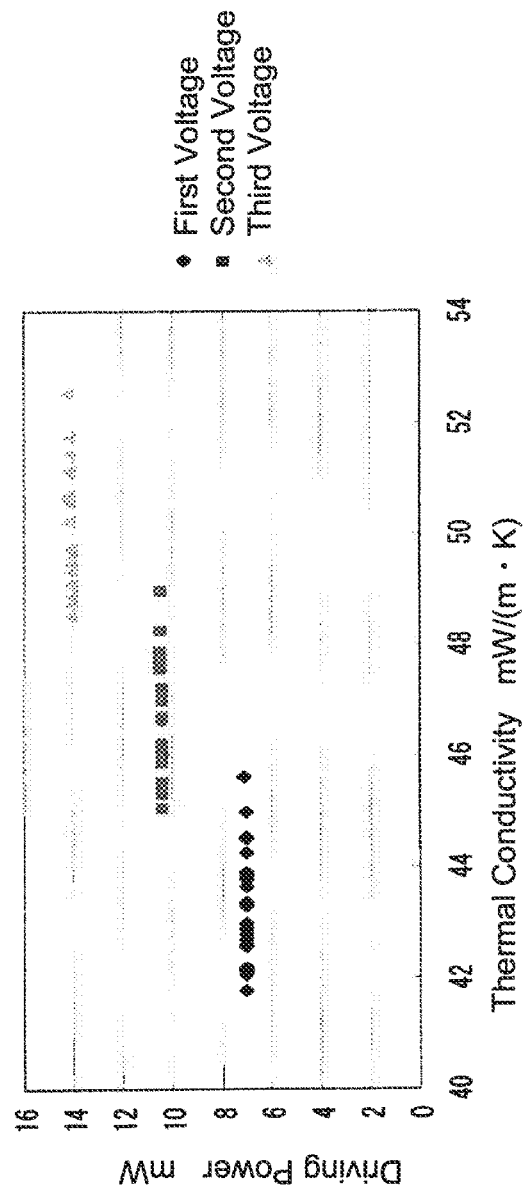
FIG. 13 is a first graph illustrating the relationship between the thermal conductivities and the driving powers of the heating elements in an example according to the present invention.
Figure 14:
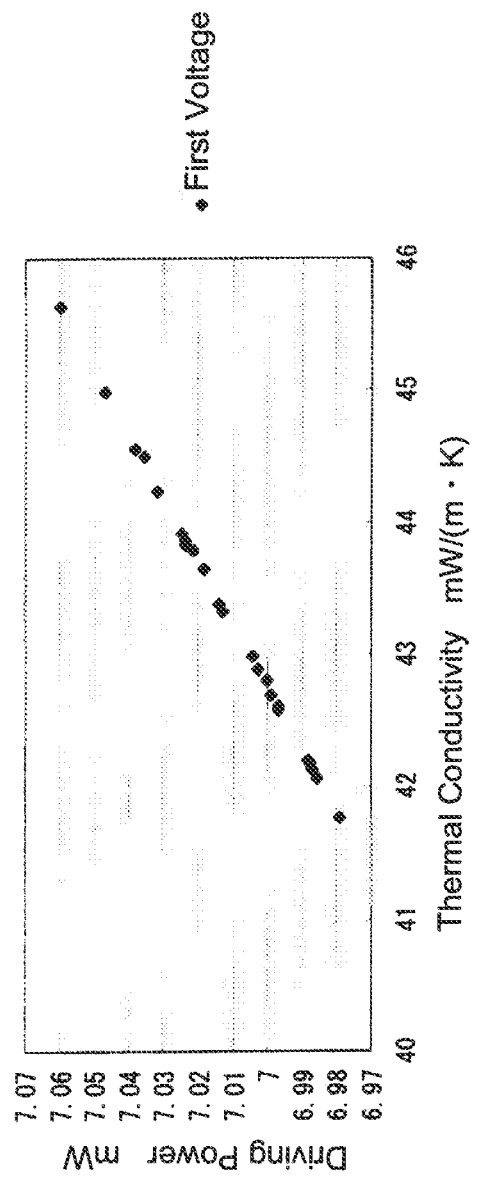
FIG. 14 is a second graph illustrating the relationship between the thermal conductivities and the driving powers of the heating elements in another example according to the present invention.

The radiation coefficient $M_I$ of the mixed gas, as indicated in Equation (4), above, is proportional to the inverse ($1/R_H$) of the resistance value $R_H$ of the heating element 61. As described above, the radiation coefficient and the thermal conductivity have a proportional relationship. Because of this, the inverse ($1/R_H$) of the resistance value $R_H$ of the heating element 61 and the thermal conductivity have a proportional relationship. FIG. 9 is a graph of the relationship between the thermal conductivity and the inverse ($1/R_H$) of the resistance value $R_H$ of the heating element 61 when the first voltage $V_1$, the second voltage $V_2$, and the third voltage $V_3$ are applied to the heating element 61. As illustrated in FIG. 9 and FIG. 10, the thermal conductivity and the inverse ($1/R_H$) of the resistance value $R_H$ of the heating element 61 have a proportional relationship as long as the voltage applied to the heating element 61 is held constant. Moreover, as illustrated in FIG. 11 and FIG. 12, there is a correlation between the thermal conductivity and the resistance value $R_H$ of the heating element 61 as long as the voltage applied to the heating element 61 is held constant. Furthermore, as illustrated in FIG. 13 and FIG. 14, there is a correlation between the thermal conductivity and the driving power of the heating element 61 as long as the voltage applied to the heating element 61 is held constant.

Consequently, defining the inverse of the resistance value of the heating element 61 when in contact with the gas A as $1/R_{HA}$, the inverse of the resistance value of the heating element 61 when in contact with the gas B as $1/R_{HB}$, the inverse of the resistance value of the heating element 61 when in contact with the gas C as $1/R_{HC}$, and the inverse of the resistance value of the heating element 61 when in contact with the gas D as $1/R_{HD}$, Equation (12), above, is rewritten, and the inverse of the resistance value of the heating element 61 when in contact with the mixed gas, $1/R_{HI}$, is given by the sum of the products of the inverses of the resistance values $R_H$ of the heating element 61 when in contact with the individual gas components multiplied by the volume fractions of those respective gas components. As a result, when a constant voltage is applied, the inverse ($1/R_H$) of the resistance value $R_H$ of the heating element 61 that is in contact with the mixed gas is given by Equation (24), below.

$$1/R_{HI} = 1/R_{HA} \times V_A + 1/R_{HB} \times V_B + 1/R_{HC} \times V_C + 1/R_{HD} \times V_D \quad (24)$$

Moreover, because the resistance value $R_H$ of the heating element 61 is dependent on the temperature $T_H$ of the heating element 61, the inverse ($1/R_H$) of the resistance value $R_H$ of the heating element 61 that is in contact with the mixed gas is given by Equation (25), below, as a function of the temperature $T_H$ of the heating element 61:

$$1/R_{HI}(T_H) = 1/R_{HA}(T_H) \times V_A + 1/R_{HB}(T_H) \times V_B + 1/R_{HC}(T_H) \times V_C + 1/R_{HD}(T_H) \times V_D \quad (25)$$

Consequently, when the temperature of the heating element 61 is $T_{H1}$, then the inverse $(1/R_{H1})$ of the resistance value $R_H$ of the heating element 61 that is in contact with the mixed gas is given by Equation (26), below. Moreover, when the temperature of the heating element 61 is $T_{H2}$, then the inverse $(1/R_{H2})$ of the resistance value $R_H$ of the heating element 61 that is in contact with the mixed gas is given by Equation (27), below, and when the temperature of the heating element 61 is $T_{H3}$, then the inverse $(1/R_{H3})$ of the resistance value $R_H$ of the heating element 61 that is in contact with the mixed gas is given by Equation (28), below.

$$1/R_{HI1}(T_{H1}) = 1/R_{HA}(T_{H1}) \times V_A + 1/R_{HB}(T_{H1}) \times V_B + 1/R_{HC}(T_{H1}) \times V_C + 1/R_{HD}(T_{H1}) \times V_D \quad (26)$$

$$1/R_{HI2}(T_{H1}) = 1/R_{HA}(T_{H2}) \times V_A + 1/R_{HB}(T_{H2}) \times V_B + 1/R_{HC}(T_{H2}) \times V_C + 1/R_{HD}(T_{H2}) \times V_D \quad (27)$$

$$1/R_{HI3}(T_{H3}) = 1/R_{HA}(T_{H3}) \times V_A + 1/R_{HB}(T_{H3}) \times V_B + 1/R_{HC}(T_{H3}) \times V_C + 1/R_{HD}(T_{H3}) \times V_D \quad (28)$$

The values of the resistances $R_{HA}(T_{H1})$, $R_{HB}(T_{H1})$, $R_{HC}(T_{H1})$, $R_{HD}(T_{H1})$, $R_{HA}(T_{H2})$, $R_{HB}(T_{H2})$, $R_{HC}(T_{H2})$, $R_{HD}(T_{H2})$, $R_{HA}(T_{H3})$, $R_{HB}(T_{H3})$, $R_{HC}(T_{H3})$, $R_{HD}(T_{H3})$ for the heating element 61 when in contact with the individual gas components in Equation (26) through Equation (28) can be obtained in advance through measurements, or the like. Consequently, when the system of simultaneous equations of Equation (10) and Equation (26) through Equation (28) is solved, the volumetric fraction $V_A$ of the gas A, the volumetric fraction $V_B$ of the gas B, the volumetric fraction $V_C$ of the gas C, and the volumetric fraction $V_D$ of the gas D, respectively, are obtained as functions of the resistance values $R_{HI1}(T_{H1})$, $R_{HI2}(T_{H2})$, and $R_{HI3}(T_{H3})$ of the heating element 61 that is in contact with the mixed gas, as shown in Equation (29) through Equation (32), below. Note that in Equations (29) through (32), below, $f_n$, where n is a non-negative integer, is a code representing a function:

$$V_A = f_5[1/R_{HI1}(T_{H1}), 1/R_{HI2}(T_{H2}), 1/R_{HI3}(T_{H3})] \quad (29)$$

$$V_B = f_6[1/R_{HI1}(T_{H1}), 1/R_{HI2}(T_{H2}), 1/R_{HI3}(T_{H3})] \quad (30)$$

$$V_C = f_7[1/R_{HI1}(T_{H1}), 1/R_{HI2}(T_{H2}), 1/R_{HI3}(T_{H3})] \quad (31)$$

$$V_D = f_8[1/R_{HI1}(T_{H1}), 1/R_{HI2}(T_{H2}), 1/R_{HI3}(T_{H3})] \quad (32)$$

Here Equation (33), below, is obtained through substituting Equation (29) through (32) into Equation (11), above.

$$\begin{aligned} Q &= K_A \times V_A + K_B \times V_B + K_C \times V_C + K_D \times V_D \\ &= K_A \times f_5[1/R_{HI1}(T_{H1}), 1/R_{HI2}(T_{H2}), 1/R_{HI3}(T_{H3})] + \\ &\quad K_B \times f_6[1/R_{HI1}(T_{H1}), 1/R_{HI2}(T_{H2}), 1/R_{HI3}(T_{H3})] + \\ &\quad K_C \times f_7[1/R_{HI1}(T_{H1}), 1/R_{HI2}(T_{H2}), 1/R_{HI3}(T_{H3})] + \\ &\quad K_D \times f_8[1/R_{HI1}(T_{H1}), 1/R_{HI2}(T_{H2}), 1/R_{HI3}(T_{H3})] \end{aligned} \quad (33)$$

As shown in Equation (33), above, the per-unit-volume calorific value Q is obtained as an equation which has, as variables, the resistance values $R_{HI1}(T_{H1})$, $R_{HI2}(T_{H2})$, and $R_{HI3}(T_{H3})$ of the heating element 61 when the temperatures of the heating element 61 are $T_{H1}$, $T_{H2}$, and $T_{H3}$. Consequently, the calorific value Q of the mixed gas is given by Equation (34), below, where $g_2$ and $g_3$ are codes representing functions.

$$\begin{aligned} Q &= g_2[1/R_{HI1}(T_{H1}), 1/R_{HI2}(T_{H2}), 1/R_{HI3}(T_{H3})] + \\ &= g_3[R_{HI1}(T_{H1}), R_{HI2}(T_{H2}), R_{HI3}(T_{H3})] \end{aligned} \quad (34)$$

Consequently, the inventors discovered that, for a mixed gas comprising a gas A, a gas D, a gas C, and a gas D, wherein the volume fraction $V_A$ of the gas A, the volume fraction $V_B$ of the gas B, the volume fraction $V_C$ of the gas C, and the volume fraction $V_D$ of the gas D, are unknown, it is possible to calculate easily the per-unit-volume calorific value of the mixed gas to be measured if Equation (34) is obtained in advance. Specifically, it is possible to calculate uniquely the calorific value Q of the mixed gas to be measured, through measuring the resistance values $R_{HI1}(T_{H1})$, $R_{HI2}(T_{H2})$, and $R_{HI3}(T_{H3})$ of the heating element 61 at the heat producing temperatures of $T_{H1}$, $T_{H2}$, and $T_{H3}$, and then substituting, into Equation (34). Moreover, in this case, the calorific value Q of the mixed gas can be measured using the heating element 61 alone, without using the first temperature measuring element 62 of the microchip 8.

Furthermore, given the correlation between the resistance R and the electric current I, the per-unit-volume calorific value Q is given by Equation (35), below, which, when $g_4$ is a code indicating a function, has as variables, the currents $I_{H1}(T_{H1})$, $I_{H2}(T_{H2})$, and $I_{H3}(T_{H3})$ flowing in the heating element 61 when the temperatures of the heating element 61 are $T_{H1}$, $T_{H2}$, and $T_{H3}$.

$$Q = g_4[I_{H1}(T_{H1}), I_{H2}(T_{H2}), I_{H3}(T_{H3})] \quad (35)$$

Furthermore, given the correlation between the resistance R of the heating element 61 and the output signal AD of the analog-digital converting circuit (hereinafter termed an "A/D converting circuit") that is connected to the heating element 61, the per-unit-volume calorific value Q of the mixed gas is given by Equation (36), below, wherein, when $g_5$ is a code indicating a function, has as variables, the output signals $AD_{H1}(T_{H1})$, $AD_{H2}(T_{H2})$, and $AD_{H3}(T_{H3})$ from the A/D converting circuit when the temperatures of the heating element 61 are $T_{H1}$, $T_{H2}$, and $T_{H3}$.

$$Q = g_5[AD_{H1}(T_{H1}), AD_{H2}(T_{H2}), AD_{H3}(T_{H3})] \quad (36)$$

Consequently, when $g_6$ is a code indicating a function, the per-unit-volume calorific value Q of a mixed gas can also be obtained from an equation having, as variables, the electric signals $S_{H1}(T_{H1})$, $S_{H2}(T_{H2})$, and $S_{H3}(T_{H3})$ from the heating element 61 when the heat producing temperatures of the heating element 61 are $T_{H1}$, $T_{H2}$, and $T_{H3}$, as shown in Equation (37), below.

$$Q = g_6[S_{H1}(T_{H1}), S_{H2}(T_{H2}), S_{H3}(T_{H3})] \quad (37)$$

Note that the gas components of the mixed gas are not limited to four different components. For example, if the mixed gas comprises n types of gas components and the symbol $g_7$ indicating a function, then first a formula, given by Equation (38), below, is obtained using, as variables, the electric signals $S_{H1}(T_{H1})$, $S_{H2}(T_{H2})$, $S_{H3}(T_{H3})$, ..., $S_{Hn-1}(T_{Hn-1})$ from the heating element 61 at at least n−1 different the heat producing temperatures $T_{H1}$, $T_{H2}$, $T_{H3}$, ..., $T_{Hn-1}$. Given this, the per-unit-volume calorific value Q of the mixed gas to be measured can be calculated uniquely by measuring the values of the electric signals $S_{H1}(T_{H1})$, $S_{H2}(T_{H2})$, $S_{H3}(T_{H3})$, ..., $S_{Hn-1}(T_{Hn-1})$ from the heating element 61, which contacts the mixed gas to be measured that comprises n different component gases for which the respective volume fractions are unknown, and then substituting into Equation (38).

$$Q = g_7[S_{H1}(T_{H1}), S_{H2}(T_{H2}), S_{H3}(T_{H3}), \ldots, S_{Hn-1}(T_{Hn-1})] \quad (38)$$

Note that if the mixed gas includes an alkane ($C_jH_{2j+2}$) other than methane ($CH_4$) and propane ($C_3H_8$), where j is a natural number, in addition to methane ($CH_4$) and propane ($C_3H_8$), then the alkane ($C_jH_{2j+2}$) other than methane ($CH_4$) and propane ($C_3H_8$) will be seen as a mixture of methane ($CH_4$) and propane ($C_3H_8$), and there will be no effect on the calculation in Equation (38). For example, as indicated in Equations (39) through (42), below, the calculation may be performed using Equation (38) by viewing ethane ($C_2H_6$), butane ($C_4H_{10}$), pentane ($C_5H_{12}$), and hexane ($C_6H_{14}$) as a mixture of methane ($CH_4$) and propane ($C_3H_8$), with each multiplied by the respective specific factors.

$$C_2H_6 = 0.5CH_4 + 0.5C_3H_8 \quad (39)$$

$$C_4H_{10} = -0.5CH_4 + 1.5C_3H_8 \quad (40)$$

$$C_5H_{12} = -1.0CH_4 + 2.0C_3H_8 \quad (41)$$

$$C_6H_{14} = -1.5CH_4 + 2.5C_3H_8 \quad (42)$$

Consequently, with z as a natural number, if a mixed gas comprising n types of gas components includes, as gas components, z types of alkanes ($C_jH_{2j+2}$) other than methane ($CH_4$) and propane ($C_3H_8$), in addition to methane ($CH_4$) and propane ($C_3H_8$), an equation may be calculated having, as variables, the electric signal $S_H$ of the heating element 61 at, at least, n−z−1 different heat producing temperatures.

Note that if the types of gas components in the mixed gas used in the calculation in Equation (38) are the same as the types of gas components of the mixed gas to be measured, wherein the per-unit-volume calorific value Q is unknown, then, of course, Equation (38) can be used in calculating the per-unit-volume calorific value Q of the mixed gas to be measured. Furthermore, Equation (38) can also be used when the mixed gas to be measured comprises a number of gas components that is less than n, where the gas components of the less than n different types are included in the mixed gas that was used for calculating Equation (38). If, for example, the mixed gas used in calculating Equation (38) included four types of gas components, namely methane ($CH_4$), propane ($C_3H_8$), nitrogen ($N_2$) and carbon dioxide ($CO_2$), then even if the mixed gas to be measured includes only three different components, namely methane ($CH_4$), propane ($C_3H_8$), and carbon dioxide ($CO_2$), without containing the nitrogen ($N_2$), still Equation (38) can be used in calculating the calorific value Q of the mixed gas to be measured.

Furthermore, if the mixed gas used in calculating Equation (38) included methane ($CH_4$) and propane ($C_3H_8$) as gas components, Equation (38) could still be used even when the mixed gas to be measured includes an alkane ($C_jH_{2j+2}$) that was not included in the mixed gas that was used in calculating Equation (38). This is because, as described above, even if the alkane ($C_jH_{2j+2}$) other than methane ($CH_4$) and propane ($C_3H_8$) is viewed as a mixture of methane ($CH_4$) and propane ($C_3H_8$) there is no effect on calculating the per-unit-volume calorific value Q using Equation (38).

Figure 15:
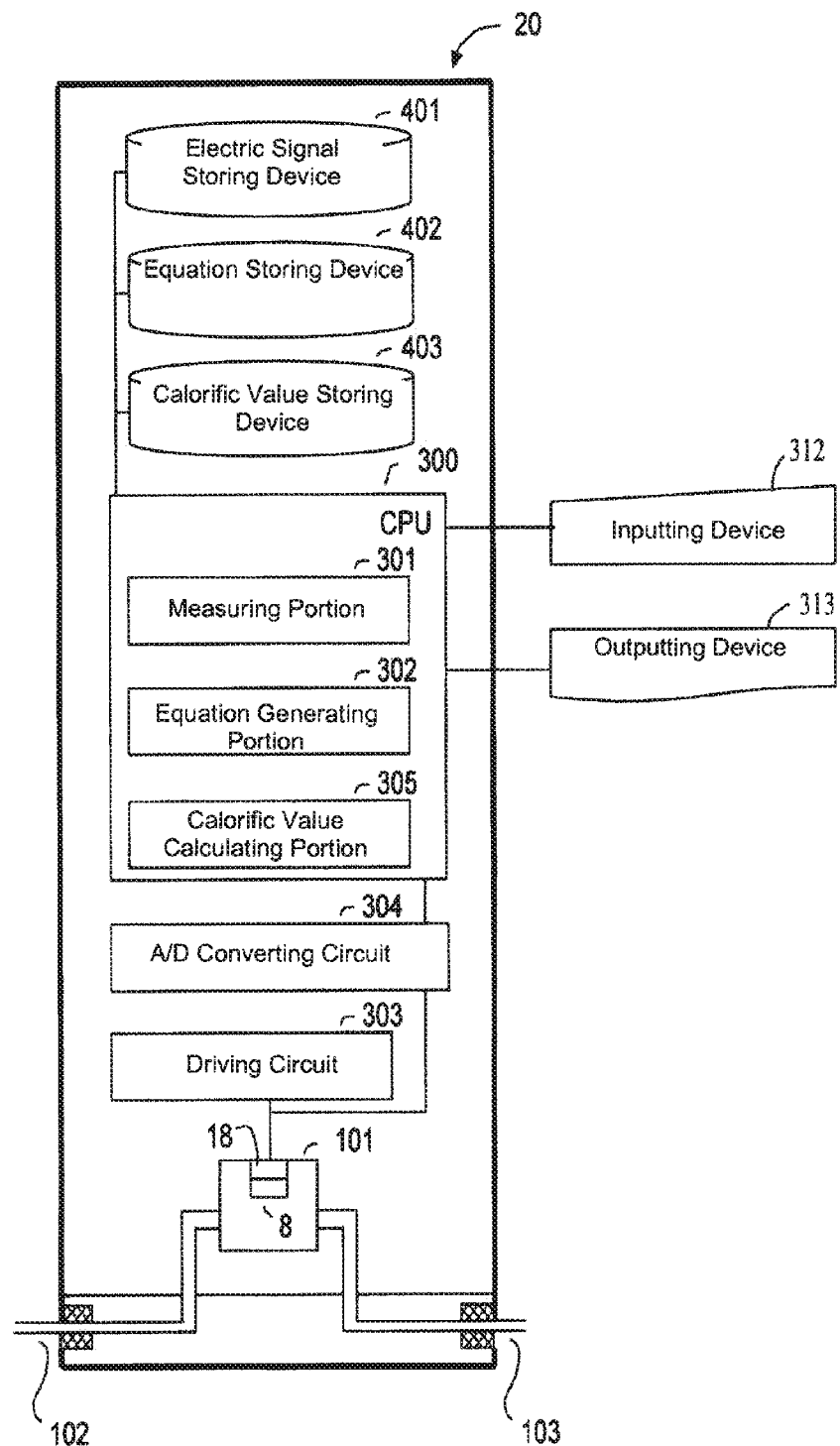
FIG. 15 is a schematic diagram of a calorific value measuring system as set forth in an example according to the present invention.
Figure 16:
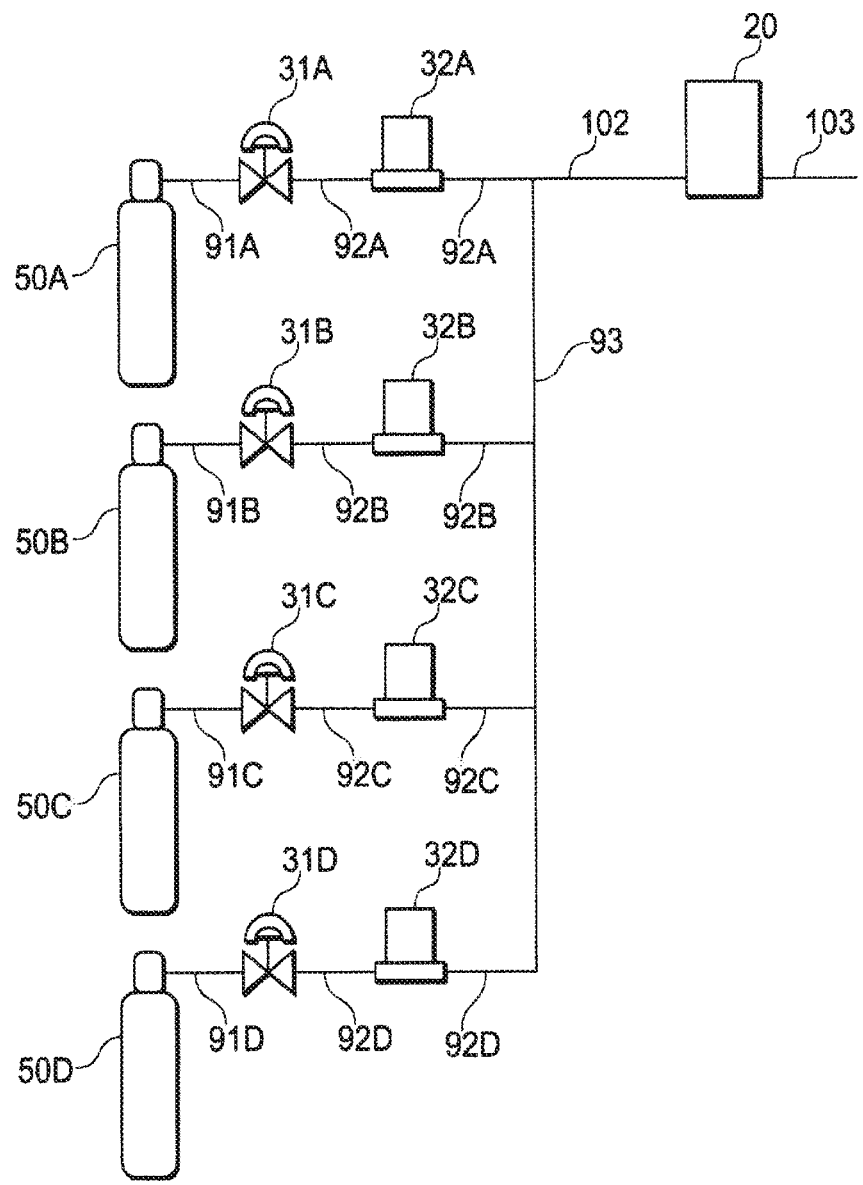
FIG. 16 is another schematic diagram of a calorific value measuring system as set forth in another example according to the present invention.

Here the calorific value measuring system 20 according to the example illustrated in FIG. 15 and FIG. 16 comprises: a chamber 101 that is a container into which each of the plurality of sample mixed gases is filled; and, disposed within the chamber 101, a microchip 8 that includes the heating element 61, as illustrated in FIG. 1 or FIG. 3, for producing heat at a plurality of heat producing temperatures $T_H$. In the below, an example is explained wherein the calorific value measuring system 20 is provided with the microchip 8 illustrated in FIG. 1; however, even if the calorific value measuring system 20 were provided with the microchip 8 illustrated in FIG. 3, the operation can be the same as with the calorific value measuring system 20 illustrated in FIG. 15.

The microchip 8 is disposed within the chamber 101, by means of a thermally insulating member 18. A flow path 102, for feeding the sample mixed gasses into the chamber 101, and a flow path 103, for discharging the sample mixed gasses from the chamber 101, are connected to the chamber 101.

The calorific value measuring system 20 further includes a measuring portion 301, for measuring values of electric signals $S_H$ from the heating element 61 that is in contact with the plurality of sample mixed gases and that produces heat at each of the plurality of heat producing temperatures $T_H$; and an equation generating portion 302 for generating a calorific value calculating equation based on known calorific values Q of a plurality of sample mixed gases and the values for the electric signals $S_H$ from the heating element 61 at the plurality of heat producing temperatures $T_H$, having the electric signals $S_H$ from the heating element 61 at the plurality of heat producing temperatures $T_H$ as independent variables, and having the calorific value Q as the dependent variable. Note that the sample mixed gasses include a plurality of types of gases.

When a four types of sample mixed gases, each having a different calorific value Q, are used, then, as illustrated in FIG. 16, a first gas canister 50A for storing a first sample mixed gas, a second gas canister 50B for storing a second sample mixed gas, a third gas canister 50C for storing a third sample mixed gas, and a fourth gas canister 50D for storing a fourth sample mixed gas are prepared. The first gas canister 50A is connected, through a flow path 91A to a first gas pressure regulating device 31A for providing the first sample mixed gas from the first gas canister 50A, regulated to a low-pressure such as, for example, 0.2 MPa. Additionally, a first flow rate controlling device 32A is connected through a flow path 92A to the first gas pressure regulating device 31A. The first flow rate controlling device 32A controls the rate of flow of the first sample mixed gas that is fed into the calorific value measuring system 20 through the flow paths 92A and 102.

A second gas pressure regulating device 31B is connected through a flow path 91B to the second gas canister 50B. Additionally, a second flow rate controlling device 32B is connected through a flow path 92B to the second gas pressure regulating device 31B. The second flow rate controlling device 32B controls the rate of flow of the second sample mixed gas that is fed into calorific value measuring system 20 through the flow paths 92B, 93, and 102.

A third gas pressure regulating device 31C is connected through a flow path 91C to the third gas canister 50C. Additionally, a third flow rate controlling device 32C is connected through a flow path 92C to the third gas pressure regulating device 31C. The third flow rate controlling device 32C controls the rate of flow of the third sample mixed gas that is fed into calorific value measuring system 20 through the flow paths 92C, 93, and 102.

A fourth gas pressure regulating device $31_D$ is connected through a flow path 91D to the fourth gas canister 50D. Additionally, a fourth flow rate controlling device 32D is connected through a flow path 92D to the fourth gas pressure regulating device 31D. The fourth flow rate controlling device 32D controls the rate of flow of the fourth sample mixed gas that is fed into calorific value measuring system 20 through the flow paths 92D, 93, and 102.

The first through fourth at sample mixed gases are each, for example, natural gas. The first through fourth sample mixed gases each include four different gas components of, for example, methane ($CH_4$), propane ($C_3H_8$), nitrogen ($N_2$), and carbon dioxide ($CO_2$).

Following this, when the first sample gas is supplied to the chamber 101, illustrated in FIG. 15, the heating element 61 illustrated in FIG. 1 and FIG. 2 applies sequentially driving powers $P_{H1}$, $P_{H2}$, and $P_{H3}$ from the driving circuit 303 illustrated in FIG. 15. When the driving powers $P_{H1}$, $P_{H2}$, and $P_{H3}$ are applied, the heating element 61 that is in contact with the first sample mixed gas produces heat at a temperature $T_{H1}$ of 100° C., a temperature $T_{H2}$ of 150° C., and a temperature $T_{H3}$ of 200° C., for example, to output an electric signal $S_{H1}$ ($T_{H1}$) at the heat producing temperature $T_{H1}$, an electric signal $S_{H2}$ ($T_{H2}$) at the heat producing temperature $T_{H2}$, and an electric signal $S_{H3}$ ($T_{H3}$) at the heat producing temperature $T_{H3}$.

After the removal of the first sample mixed gas from the chamber 101, the second through fourth sample mixed gases are supplied sequentially into the chamber 101. When a second simple mixed gas is provided into the chamber 101, the heating element 61, illustrated in FIG. 1 and FIG. 2, which is in contact with the second sample mixed gas, outputs an electric signal $S_{H1}$ ($T_{H1}$) at a heat producing temperature $T_{H1}$, an electric signal $S_{H2}$ ($T_{H2}$) at a heat producing temperature $T_{H2}$, and an electric signal $S_{H3}$ ($T_{H3}$) at a heat producing temperature $T_{H3}$. When a third simple mixed gas is provided into the chamber 101, illustrated in FIG. 15, the heating element 61, illustrated in FIG. 1 and FIG. 2, which is in contact with the third sample mixed gas, outputs an electric signal $S_{H1}$ ($T_{H1}$) at a heat producing temperature $T_{H1}$, an electric signal $S_{H2}$ ($T_{H2}$) at a heat producing temperature $T_{H2}$, and an electric signal $S_{H3}$ ($T_{H3}$) at a heat producing temperature $T_{H3}$. When a fourth simple mixed gas is provided into the chamber 101, illustrated in FIG. 15, the heating element 61, illustrated in FIG. 1 and FIG. 2, which is in contact with the fourth sample mixed gas, outputs an electric signal $S_{H1}$ ($T_{H1}$) at a heat producing temperature $T_{H1}$, an electric signal $S_{H2}$ ($T_{H2}$) at a heat producing temperature $T_{H2}$, and an electric signal $S_{H3}$ ($T_{H3}$) at a heat producing temperature $T_{H3}$.

Note that if there are n types of gas components in each of the sample mixed gases, the heating element 61 of the microchip 8, illustrated in FIG. 1 and FIG. 2, is caused to produce heat at at least n−1 different temperatures. However, as described above, an alkane ($C_jH_{2j+2}$) other than methane ($CH_4$) and propane ($C_3H_8$) can be viewed as a mixture of methane ($CH_4$) and propane ($C_3H_8$). Consequently, with z as a natural number, if a sample mixed gas comprising n types of gas components includes, as gas components, z types of alkanes ($C_jH_{2j+2}$) in addition to methane ($CH_4$) and propane ($C_3H_8$), the heating element 61 is caused to produce heat at n−z−1 different temperatures.

As illustrated in FIG. 15, the microchip 8 is connected to a central calculation processing device (CPU) 300 that includes the measuring portion 301. An electric signal storage device 401 is also connected to the CPU 300. The measuring portion 301 measures the values of the electric signal $S_{H1}$ ($T_{H1}$) at the heat producing temperature $T_{H1}$, the electric signal $S_{H2}$ ($T_{H2}$) at the heat producing temperature $T_{H2}$, and the electric signal $S_{H3}$ ($T_{H3}$) at the heat producing temperature $T_{H3}$, from the heating element 61, and stores the measured values in the electric signal storage device 401. Note that an electric signal $S_H$ from the heating element 61 may be the resistance value $R_H$ of the heating element 61, the current $I_H$ flowing in the heating element 61, or the output signal $AD_H$ from the A/D converting circuit 304 that is connected to the heating element 61.

The equation generating portion 302 that is included in the CPU 300 collects the respective known values for the calorific values Q of, for example, each of the first through fourth sample mixed gases and the plurality of measured values for the electric signals $S_{H1}$ ($T_{H1}$), $S_{H2}$ ($T_{H2}$), and $S_{H3}$ ($T_{H3}$) from the heating element 61. Moreover, the equation generating portion 302 calculates a calorific value calculating equation, through Multivariate statistics, based on the collected values for the calorific values Q and electric signals $S_H$, with the electric signals $S_{H1}(T_{H1})$, $S_{H2}(T_{H2})$, and $S_{H3}(T_{H3})$ from the heating element 61 as the independent variables and the calorific value Q as the dependent variable.

Note that "Multivariate statistics" includes support vector analysis disclosed in A. J. Smola and B. Scholkopf (eds.), "A Tutorial on Support Vector Regression" (NeuroCOLT Technical Report NC-TR-98-030), multiple linear regression analysis, the Fuzzy Quantification Theory Type II, disclosed in Japanese Unexamined Patent Application Publication H5-141999, and the like.

The calorific value measuring system 20 is further provided with an equation storage device 402, connected to the CPU 300. The equation storage device 402 stores the calorific value calculating equation generated by the equation generating portion 302. An inputting device 312 and an outputting device 313 are also connected to the CPU 300. A keyboard, a pointing device such as a mouse, or the like, may be used as the inputting device 312. An image displaying device such as a liquid crystal display or a monitor, or a printer, or the like, may be used as the outputting device 313.

Figure 17:
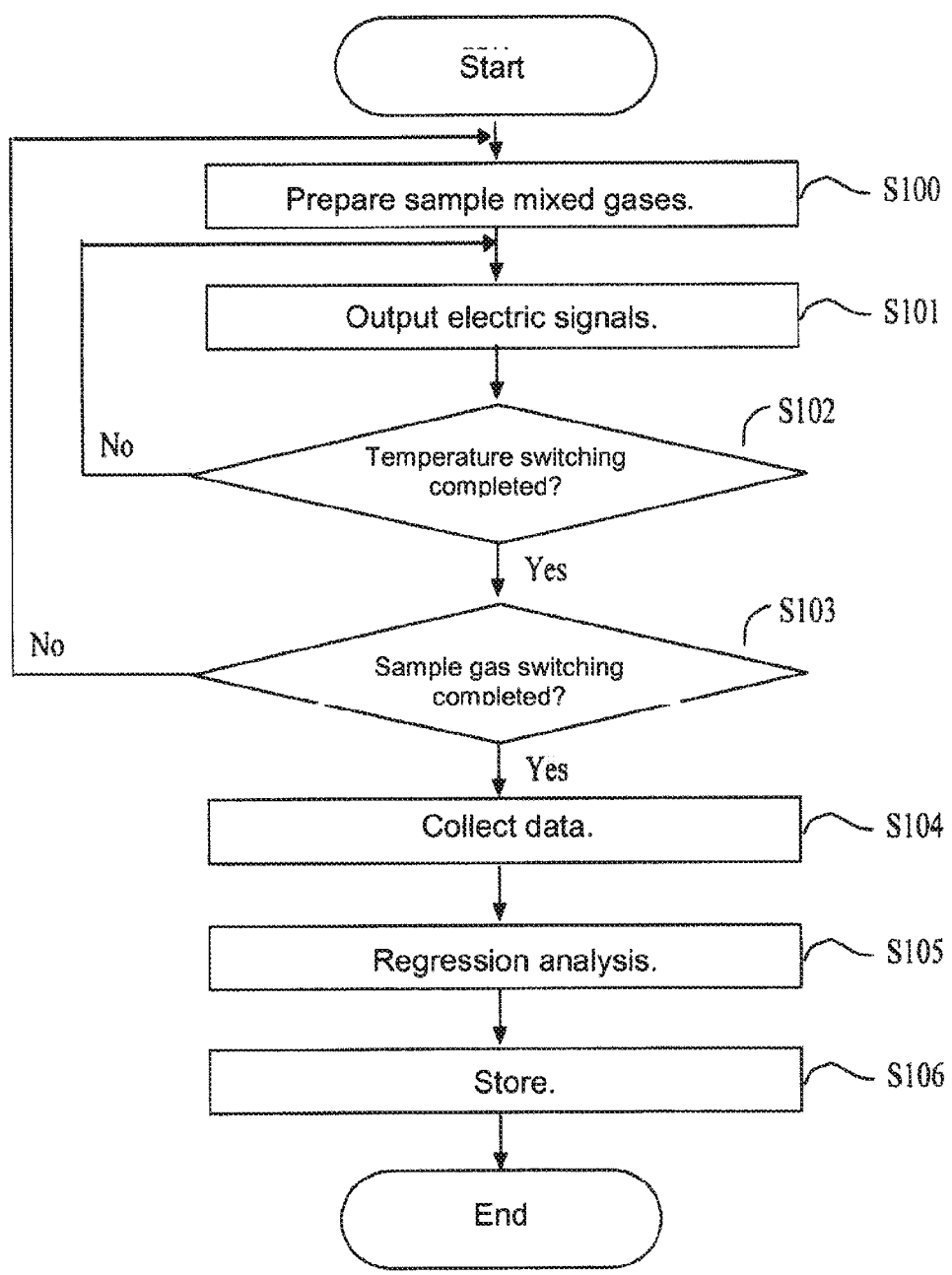
FIG. 17 is a flowchart illustrating a method for generating a calorific value calculating equation as set forth in an example.

The flowchart in FIG. 17 is used next to explain a method for generating a calorific value calculating equation as set forth in a form of embodiment.

(a) In Step S100, the valve for the first flow rate controlling device 32A is opened while leaving the second through fourth flow rate controlling devices 32B through 32D, illustrated in FIG. 16, closed, to introduce the first sample mixed gas into the chamber 101 illustrated in FIG. 15. In Step S101, the driving circuit 303 applies a driving power $P_{H1}$ to the heating element 61 illustrated in FIG. 1 and FIG. 2, to cause the heating element 61 produce heat at 100° C. The measuring portion 301, illustrated in FIG. 15, measures the value of the electric signal $S_{H1}(T_{H1})$ from the heating element 61 that produces heat at 100° C. and stores it into the electric signal storage device 401.

(b) In Step S102, the driving circuit 303 evaluates whether or not the switching of the temperatures of the heating element 61, illustrated in FIG. 1 and FIG. 2, has been completed. If the switching to the temperature of 150° C. and to the temperature of 200° C. has not been completed, then processing returns to Step S101, and the driving circuit 303, illustrated in FIG. 15, causes the heating element 61, illustrated in FIG. 1 and FIG. 2, to produce heat at 150° C. The measuring portion 301, illustrated in FIG. 15, measures the value of the electric signal $S_{H2}(T_{H2})$ from the heating element 61 that is in contact with the first sample mixed gas and that produces heat at 150° C., and stores it into the electric signal storage device 401.

(c) In Step S102, whether or not the switching of the temperatures of the heating element 61, illustrated in FIG. 1 and FIG. 2, has been completed is evaluated again. If the switching to the temperature of 200° C. has not been completed, then processing returns to Step S101, and the driving circuit 303, illustrated in FIG. 15, causes the heating element 61, illustrated in FIG. 1 and FIG. 2, to produce heat at 200° C. The measuring portion 301, illustrated in FIG. 15, stores, into the electric signal storage device 401, the value of the electric signal $S_{H3}(T_{H3})$ from the heating element 61 that is in contact with the first sample mixed gas and that produces heat at 200° C.

(d) If the switching of the temperature of the heating element 61 has been completed, then processing advances from Step S102 to Step S103. In Step S103, an evaluation is performed as to whether or not the switching of the sample mixed gases has been completed. If the switching to the second through fourth sample mixed gases has not been completed, processing returns to Step S100. In Step S100, the valve for the first flow rate controlling device 32A is closed and the valve for the second flow rate controlling device 32B is opened while leaving the third and fourth flow rate controlling devices 32C through 32D, illustrated in FIG. 16, closed, to introduce the second sample mixed gas into the chamber 101 illustrated in FIG. 15.

(e) The loop of Step S101 through Step S102 is repeated in the same manner as for the first sample mixed gas. Moreover, the measuring portion 301 measures the values of the electric signals $S_{H1}(T_{H1})$, $S_{H2}(T_{H2})$, and $S_{H3}(T_{H3})$ from the heating element 61 that is in contact with the second sample mixed gas and that produces heat at 100° C., 150° C., and 200° C., and stores them into the electric signal storage device 401.

(f) Thereafter, the loop of Step S100 through Step S103 is repeated. As a result, the values of the electric signals $S_{H1}(T_{H1})$, $S_{H2}(T_{H2})$, and $S_{H3}(T_{H3})$ from the heating element 61 that is in contact with the third sample mixed gas and that produces heat at 100° C., 150° C., and 200° C. are stored into the electric signal storage device 401. Moreover, the values of the electric signals $S_{H1}(T_{H1})$, $S_{H2}(T_{H2})$, and $S_{H3}(T_{H3})$ from the heating element 61 that is in contact with the fourth sample mixed gas and that produces heat at 100° C., 150° C., and 200° C. are stored into the electric signal storage device 401.

(g) In Step S104, the value for the known calorific value Q of the first sample mixed gas, the value for the known calorific value Q of the second sample mixed gas, the value for the known calorific value Q of the third sample mixed gas, and the value for the known calorific value Q of the fourth sample mixed gas are inputted into the equation generating portion 302 from the inputting device 312. Moreover, the equation generating portion 302 reads out, from the electric signal storage device 401, the plurality of measured values for the electric signals $S_{H1}(T_{H1})$, $S_{H2}(T_{H2})$, and $S_{H3}(T_{H3})$ from the heating element 61.

(h) In Step S105, the equation generating portion 302 performs multiple linear regression analysis based on the values for the calorific values Q of the first through fourth sample mixed gases and the plurality of measured values for the electric signals $S_{H1}(T_{H1})$, $S_{H2}(T_{H2})$, and $S_{H3}(T_{H3})$ from the heating element 61. Through the multiple linear regression analysis, the equation generating portion 302 calculates a calorific value calculating equation having the electric signals $S_{H1}(T_{H1})$, $S_{H2}(T_{H2})$, and $S_{H3}(T_{H3})$ from the heating element 61 as the independent variables and the calorific value Q of the gas as the dependent variable. Thereafter, in Step S106, the equation generating portion 302 stores, into the equation storage device 402, the equation that has been generated, to complete the method for generating the calorific value calculating equation as set forth in the example.

As described above, the method for generating a calorific value calculating equation as set forth in the example enables the generation of a calorific value calculating equation that calculates a unique value for the calorific value Q of a mixed gas being measured.

The functions of a calorific value measuring system 20 when measuring the calorific value Q of a mixed gas wherein calorific value Q is unknown is explained next. For example, a mixed gas to be measured, such as a natural gas that includes, at unknown volume fractions, methane ($CH_4$), propane ($C_3H_8$), nitrogen ($N_2$), and carbon dioxide gas ($CO_2$), with an unknown calorific value Q, is introduced into the chamber 101. Following this, the heating element 61 of the microchip 8 illustrated in FIG. 1 and FIG. 2 applies sequentially driving powers $P_{H1}$, $P_{H2}$, and $P_{H3}$ from the driving circuit 303 illustrated in FIG. 15. When the driving powers $P_{H1}$, $P_{H2}$, and $P_{H3}$ are applied, the heating element 61 that is in contact with the mixed gas being measured sequentially produces heat at a temperature $T_{H1}$ of 100° C., a temperature $T_{H2}$ of 150° C., and a temperature $T_{H3}$ of 200° C., for example, to output an electric signal $S_{H1}(T_{H1})$ at the heat producing temperature $T_{H1}$, an electric signal $S_{H2}(T_{H2})$ at the heat producing temperature $T_{H2}$, and an electric signal $S_{H3}(T_{H3})$ at the heat producing temperature $T_{H3}$.

The measuring portion 301 illustrated in FIG. 15 measures the values of the electric signal $S_{H1}(T_{H1})$ at the heat producing temperature $T_{H1}$, the electric signal $S_{H2}(T_{H2})$ at the heat producing temperature $T_{H2}$, and the electric signal $S_{H3}(T_{H3})$ at the heat producing temperature $T_{H3}$, from the heating element 61, which is in contact with the mixed gas being measured, and stores the measured values in the electric signal storage device 401.

As described above, the equation storage device 402 stores a calorific value calculating equation that has, as independent variables, the electric signal $S_{H1}(T_{H1})$ from the heating element 61 with a heat producing temperature $T_{H1}$ of 100° C., the electric signal $S_{H2}(T_{H2})$ from the heating element 61 with a heat producing temperature $T_{H2}$ of 150° C., and the electric signal $S_{H3}(T_{H3})$ from the heating element 61 with a heat producing temperature $T_{H3}$ of 200° C., and that has, as the dependent variable, the calorific value Q of the gas.

The calorific value measuring system 20 according to another example also includes a calorific value calculating portion 305. The calorific value calculating portion 305 substitutes the respective measured values into the independent variables for the electric signals $S_{H1}(T_{H1})$, $S_{H2}(T_{H2})$, and $S_{H3}(T_{H3})$, from the heating element 61, of the calorific value calculating equation, to calculate the measured value of the calorific value Q of the mixed gas being measured. A calorific value storage device 403 is also connected to the CPU 300. The calorific value storage device 403 stores the value for the calorific value Q of the mixed gas to be measured, calculated by the calorific value calculating portion 305.

Figure 18:
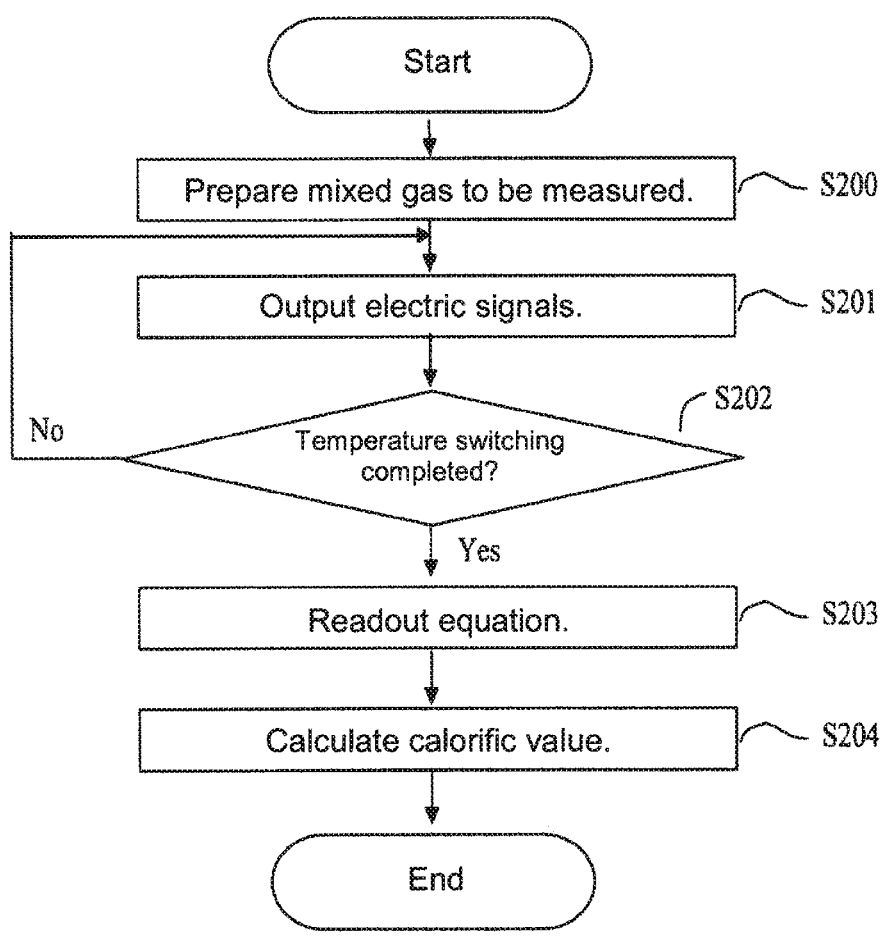
FIG. 18 is a flowchart illustrating a calorific value measuring method as set forth in another example.

The flowchart in FIG. 18 is used next to explain a method for measuring a calorific value as set forth in a further example.

(a) In Step S200, the mixed gas to be measured is introduced into the chamber 101 illustrated in FIG. 15. In Step S201, the driving circuit 303 applies a driving power $P_{H1}$ to the heating element 61 illustrated in FIG. 1 and FIG. 2, to cause the heating element 61 produce heat at 100° C. The measuring portion 301, illustrated in FIG. 15, stores, into the electric signal storage device 401, the value of the electric signal $S_{H1}(T_{H1})$ from the heating element 61 that is in contact with the mixed gas to be measured and that produces heat at 100° C.

(b) In Step S202, the driving circuit 303, illustrated in FIG. 15, evaluates whether or not the switching of the temperatures of the heating element 61, illustrated in FIG. 1 and FIG. 2, has been completed. If the switching to the temperature of 150° C. and to the temperature of 200° C. has not been completed, then processing returns to Step S201, and the driving circuit 303 applies a driving power $P_{H2}$ to the heating element 61, illustrated in FIG. 1 and FIG. 2, to cause the heating element 61 to produce heat at 150° C. The measuring portion 301, illustrated in FIG. 15, stores, into the electric signal storage device 401, the value of the electric signal $S_{H2}(T_{H2})$ from the heating element 61 that is in contact with the mixed gas to be measured and that produces heat at 150° C.

(c) In Step S202, whether or not the switching of the temperatures of the heating element 61, illustrated in FIG. 1 and FIG. 2, has been completed is evaluated again. If the switching to the temperature of 200° C. has not been completed, then processing returns to Step S201, and the driving circuit 303 applies a driving power $P_{H3}$ to the heating element 61, illustrated in FIG. 1 and FIG. 2, to cause the heating element 61 to produce heat at 200° C. The measuring portion 301, illustrated in FIG. 15, stores, into the electric signal storage device 401, the value of the electric signal $S_{H3}(T_{H3})$ from the heating element 61 that is in contact with the mixed gas to be measured and that produces heat at 200° C.

(d) If the switching of the temperature of the heating element 61 has been completed, then processing advances from Step S202 to Step S203. In Step S203, the calorific value calculating portion 305, illustrated in FIG. 15, reads out, from the equation storage device 402, a calorific value calculating equation having the electric signals $S_{H1}(T_{H1})$, $S_{H2}(T_{H2})$, and $S_{H3}(T_{H3})$ from the heating element 61 as the independent variables and the calorific value Q of the gas as the dependent variable. Moreover, the calorific value calculating portion 305 reads out, from the electric signal storage device 401, measured values for the electric signals $S_{H1}(T_{H1})$, $S_{H2}(T_{H2})$, and $S_{H3}(T_{H3})$ from the heating element 61 that is in contact with the mixed gas to be measured.

(e) In Step S204, the calorific value calculating portion 305 substitutes the respective measured values into the independent variables for the electric signals $S_{H1}(T_{H1})$, $S_{H2}(T_{H2})$, and $S_{H3}(T_{H3})$ of the calorific value calculating equation, to calculate the value of the calorific value Q of the mixed gas to be measured. Thereafter, the calorific value calculating portion 305 stores, into the calorific value storage device 403, the value calculated for the calorific value Q, to complete the method for measuring the calorific value as set forth in the example.

The calorific value calculating method according to the example described above enables the measurement of the calorific value Q of a mixed gas that is a mixed gas to be measured, from values for the electric signals $S_{H1}(T_{H1})$, $S_{H2}(T_{H2})$, and $S_{H3}(T_{H3})$ from the heating element 61 that is in contact with the mixed gas to be measured, without using costly gas chromatography equipment or speed-of-sound sensors.

The hydrocarbon compositional ratios of natural gas vary depending on the gas fields from which it is produced. Moreover, natural gas also includes nitrogen ($N_2$) and carbon dioxide gas ($CO_2$), and the like, in addition to the hydrocarbons. Because of this, the volume fractions of the gas components that are included in the natural gas will vary depending on the gas field of production, and even if the types of the gas components are known in advance, often the calorific value Q of the natural gas are unknown. Moreover, even with natural gas that derives from the same gas field, the calorific values Q are not always identical, and may vary depending on the timing of extraction.

Conventionally, when collecting natural gas usage fees, a method was used wherein the charges would be calculated based on the volume used, rather than on the calorific value Q of the natural gas used. However, because the calorific value Q varies depending on the gas field of production, from which the natural gas is derived, it is not fair to charge based on the volume used. In contrast, the use of the calorific value calculating method according to the present example makes it possible to calculate easily the calorific value Q of a mixed gas, such as a natural gas, wherein the types of the gas components are known in advance but the calorific value Q are not known because the volume fractions of the gas components are not known. This makes it possible to charge fair usage fees.

Moreover, when driving a gas turbine, there is the need to be able to monitor, without a time lag, the calorific value Q of the natural gas that is the fuel that is supplied to the gas turbine. This is because variations, or the like, in combustion may damage the gas turbine if the calorific value Q of the natural gas is not constant. However, the conventional calorimeter cannot be applied to controlling the calorific value Q of natural gas supplied to a gas turbine because the response time is long, in units of minutes. In this regard, the calorific value measuring system according to the present example makes it possible to measure the calorific value in units of seconds, enabling application to controlling the calorific value Q of natural gas that is supplied to a gas turbine.

Furthermore, the calorific value calculating method according to the example makes it easy to know the precise calorific value Q of a mixed gas such as natural gas, thus making it possible to set as appropriate the air flow rate required when burning the mixed gas. This makes it possible to reduce the amount of extraneous carbon dioxide ($CO_2$) emission.

As an example, 40 different sample mixed gases with known values for the calorific value Q were prepared. The 40 different sample mixed gases each included methane ($CH_4$), propane ($C_3H_8$), nitrogen ($N_2$), and/or carbon dioxide gas ($CO_2$) as gas components. For example, a particular sample mixed gas included 90 vol % methane, 3 vol % ethane, 1 vol % propane, 1 vol % butane, 4 vol % nitrogen, and 1 vol % carbon dioxide. Moreover, a particular sample mixed gas included 85 vol % methane, 10 vol % ethane, 3 vol % propane, and 2 vol % butane, and did not include nitrogen or carbon dioxide. Moreover, a particular sample mixed gas included 85 vol % methane, 8 vol % ethane, 2 vol % propane, 1 vol % butane, 2 vol % nitrogen, and 2 vol % carbon dioxide.

Following this, each of the 40 different sample mixed gases were used to obtain a plurality of measured values for the electric signals $S_{H1}(T_{H1})$, $S_{H2}(T_{H2})$, and $S_{H3}(T_{H3})$ from the heating element. Thereafter, a linear equation, a quadratic equation, and a cubic equation for calculating the calorific value Q were produced, based on the known values for the calorific values Q of the 40 different sample mixed gases, and the plurality of measured values for the electric signals $S_{H1}(T_{H1})$, $S_{H2}(T_{H2})$, $S_{H3}(T_{H3})$, and $S_{H4}(T_{H4})$ from the heating element, with the electric signals $S_{H1}(T_{H1})$, $S_{H2}(T_{H2})$, $S_{H3}(T_{H3})$, and $S_{H4}(T_{H4})$ from the heating element as the independent variables and the calorific value Q as the dependent variable.

When generating the a equation for calculating the calorific value Q, as a rule it is possible to determine the equation appropriately using between 3 and 5 calibration points. When generating a quadratic equation for calculating the calorific value Q, as a rule it is possible to determine the equation appropriately using between 8 and 9 calibration points. When generating a cubic equation for calculating the calorific value Q, as a rule it is possible to determine the equation appropriately using between 10 and 14 calibration points.

Figure 19:
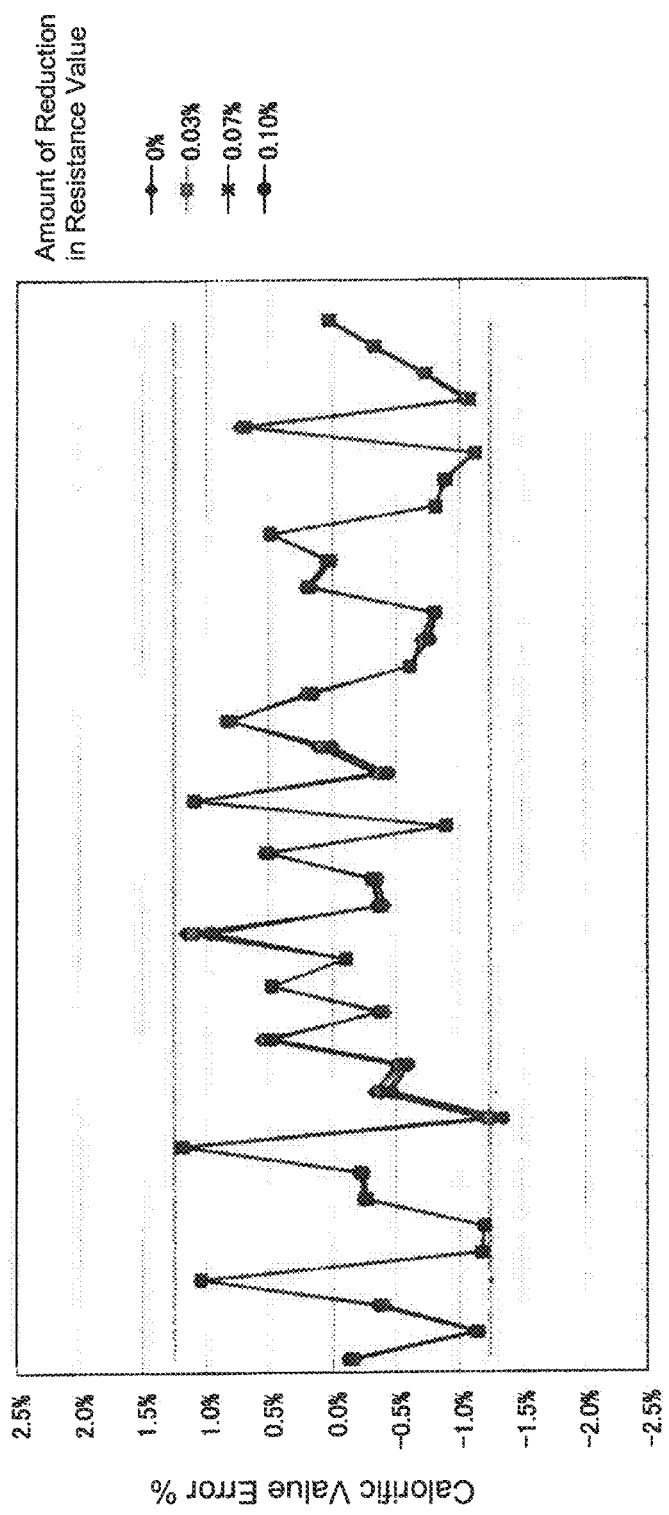
FIG. 19 is a graph showing the calorific value calculation error in an example according to the present invention.

The calorific value calculating equations that were generated were used to calculate the respective calorific values Q of the 40 different sample mixed gases, and when compared to the true calorific values Q, the error was within a range of ±1.3%, as illustrated in FIG. 19. Moreover, although the resistance of the heating element was intentionally decreased by 0.03%, 0.07%, and 0.10%, there was no increase in the amount of error. This indicates that even drift in the heating element that results from degradation over time will not affect the calculation of the calorific value.

In comparison, the radiation coefficient $M_I$ of the mixed gas, as indicated in Equation (9), above, depends on the resistance value $R_H$ of the heating element and on the resistance value $R_I$ of the temperature measuring element. Given this, the per-unit-volume calorific value Q of the thermal diffusion rate of a mixed gas can also be obtained from an equation having, as variables, the resistance values $R_{H1}(T_{H1})$, $R_{H2}(T_{H2})$, and $R_{H3}(T_{H3})$ in the heating element when the temperatures of the heating element are $T_{H1}$, $T_{H2}$, and $T_{H3}$, and the resistance value $R_I$ of the temperature measuring element that is in contact with the mixed gas, as shown in Equation (43), below.

$$Q = g[R_{H1}(T_{H1}), R_{H2}(T_{H2}), R_{H3}(T_{H3}), R_I] \quad (43)$$

Moreover, the per-unit-volume calorific value Q of the thermal diffusion rate of a mixed gas can also be obtained from an equation having, as variables, the electric currents $I_{H1}(T_{H1})$, $I_{H2}(T_{H2})$, and $I_{H3}(T_{H3})$ in the heating element when the temperatures of the heating element are $T_{H1}$, $T_{H2}$, and $T_{H3}$, and the electric current $I_I$ of the temperature measuring element that is in contact with the mixed gas, as shown in Equation (44), below.

$$Q = g[I_{H1}(T_{H1}), I_{H2}(T_{H2}), I_{H3}(T_{H2}), I_I] \quad (44)$$

Conversely, the per-unit-volume calorific value Q of the thermal diffusion rate of a mixed gas can also be obtained from an equation having, as variables, the voltages $I_{H1}(T_{H1})$, $I_{H2}(T_{H2})$, and $I_{H3}(T_{H3})$ applied to heating element when the temperatures of the heating element are $T_{H1}$, $T_{H2}$, and $T_{H3}$, and the voltage $V_I$ of the temperature measuring element that is in contact with the mixed gas, as shown in Equation (45), below.

$$Q = g[V_{H1}(T_{H1}), V_{H2}(T_{H2}), V_{H3}(T_{H3}), V_I] \quad (45)$$

Conversely, the per-unit-volume calorific value of a mixed gas can also be obtained from an equation having, as variables, the output voltages $AD_{H1}(T_{H1})$, $AD_{H2}(T_{H2})$, and $AD_{H3}(T_{H3})$ of analog-digital converting circuits (hereinafter termed "A/D converting circuits") that are connected to the heating element when the temperatures of the heating element are $T_{H1}$, $T_{H2}$, and $T_{H3}$, and the output voltage $AD_I$ of an A/D converting circuit that is connected to the temperature measuring element that is in contact with the mixed gas, as shown in Equation (46), below.

$$Q = g[AD_{H1}(T_{H1}), AD_{H2}(T_{H2}), AD_{H3}(T_{H3}), AD_I] \quad (46)$$

Consequently, the per-unit-volume calorific value Q of a mixed gas can also be obtained from an equation having, as variables, the electric signals $S_{H1}(T_{H1})$, $S_{H2}(T_{H2})$, and $S_{H3}(T_{H3})$ from the heating element when the heat producing temperatures of the heating element are $T_{H1}$, $T_{H2}$, and $T_{H3}$, and the electric signal $S_I$ of the temperature measuring element that is in contact with the mixed gas, as shown in Equation (47), below.

$$Q = g[S_{H1}(T_{H1}), S_{H2}(T_{H2}), S_{H3}(T_{H3}), S_I] \quad (47)$$

Following this, each of the same 40 different sample mixed gases as in the above examples were used to obtain a plurality of measured values for the electric signal $S_I$ from the temperature measuring element, and a plurality of measured values for the electric signals $S_{H1}(T_{H1})$, $S_{H2}(T_{H2})$, and $S_{H3}(T_{H3})$ from the heating element. Thereafter, a linear equation, a quadratic equation, and a cubic equation for calculating the calorific value Q were produced, based on the known values for the calorific values Q of the 40 different sample mixed gases, the plurality of measured values for the electric signals $S_I$ from the temperature measuring element, and the plurality of measured values for the electric signals $S_{H1}(T_{H1})$, $S_{H2}(T_{H2})$, $S_{H3}(T_{H3})$, and $S_{H4}(T_{H4})$ from the heating element, with the electric signal $S_I$ from the temperature measuring element and the values for the electric signals $S_{H1}(T_{H1})$, $S_{H2}(T_{H2})$, $S_{H3}(T_{H3})$, and $S_{H4}(T_{H4})$ from the heating element as the independent variables and the calorific value Q as the dependent variable.

Figure 20:
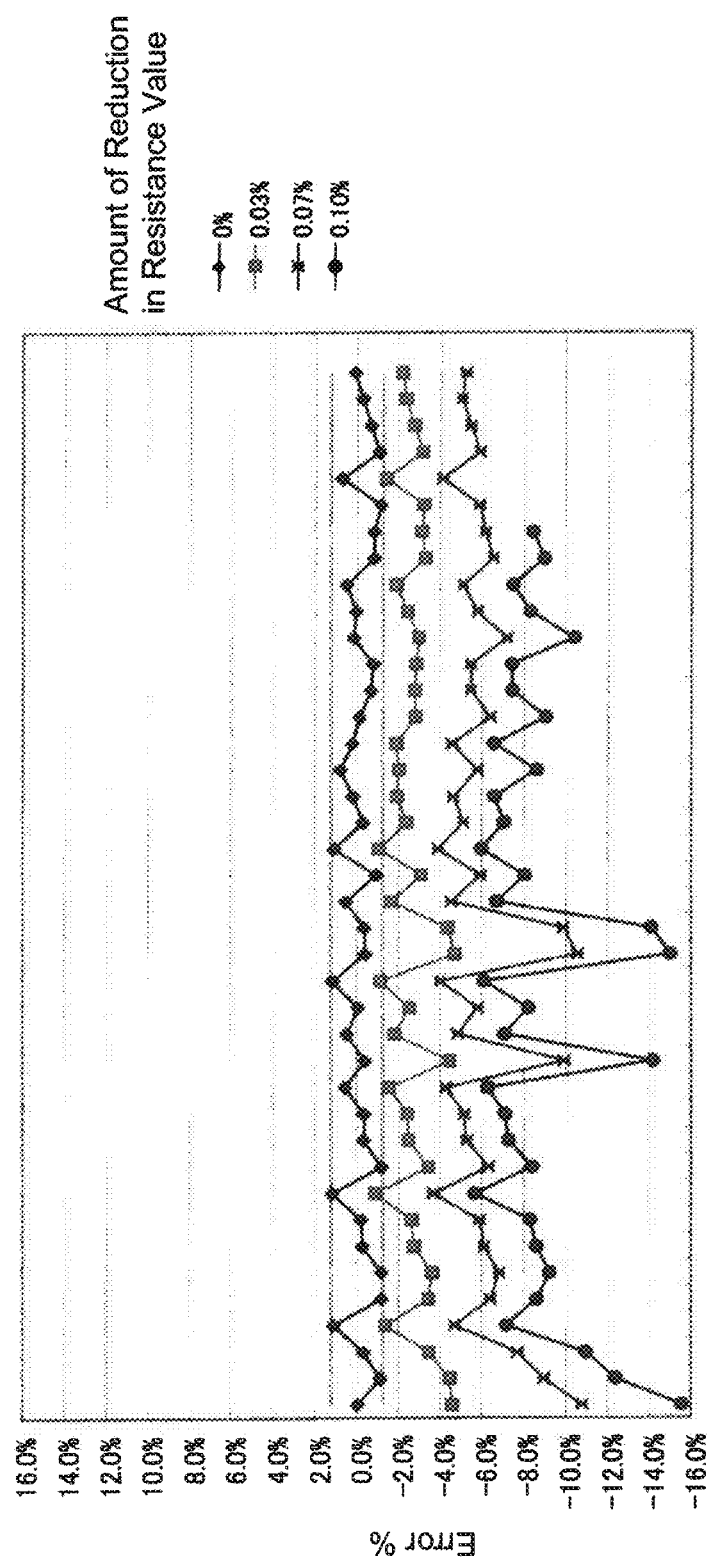
FIG. 20 is a graph showing the calorific value calculation error in a first comparative example.

The calorific value calculating equations that were generated were used to calculate the respective calorific values Q of the 40 different sample mixed gases, and when compared to the true calorific values Q, the error was within a range of ±1.3%, as illustrated in FIG. 20. However, when the resistance of the heating element was intentionally decreased by 0.03%, 0.07%, and 0.10% while keeping the resistance of the temperature measuring element constant, the amount of error increased. This indicates that drift in the heating element that results from degradation over time has an effect on the calculation of the calorific value.

As described above, the temperature measuring element carries a current to the extent that the temperature measuring element does not produce heat itself, and thus the degradation in the temperature measuring element over time is small when compared to the degradation over time in the heating element. While, when calculating the calorific value using a calorific value calculating equation that includes the electric signal $S_I$ from the temperature measuring element, it is possible to calculate the calorific value accurately as long as the temperature measuring element does not undergo degradation with the passage of time, it has been shown that if the temperature measuring element undergoes degradation with the passage of time, the differences in degradation with the passage of time in the temperature measuring element will appear as error in the calculation of the calorific value.

Figure 21:
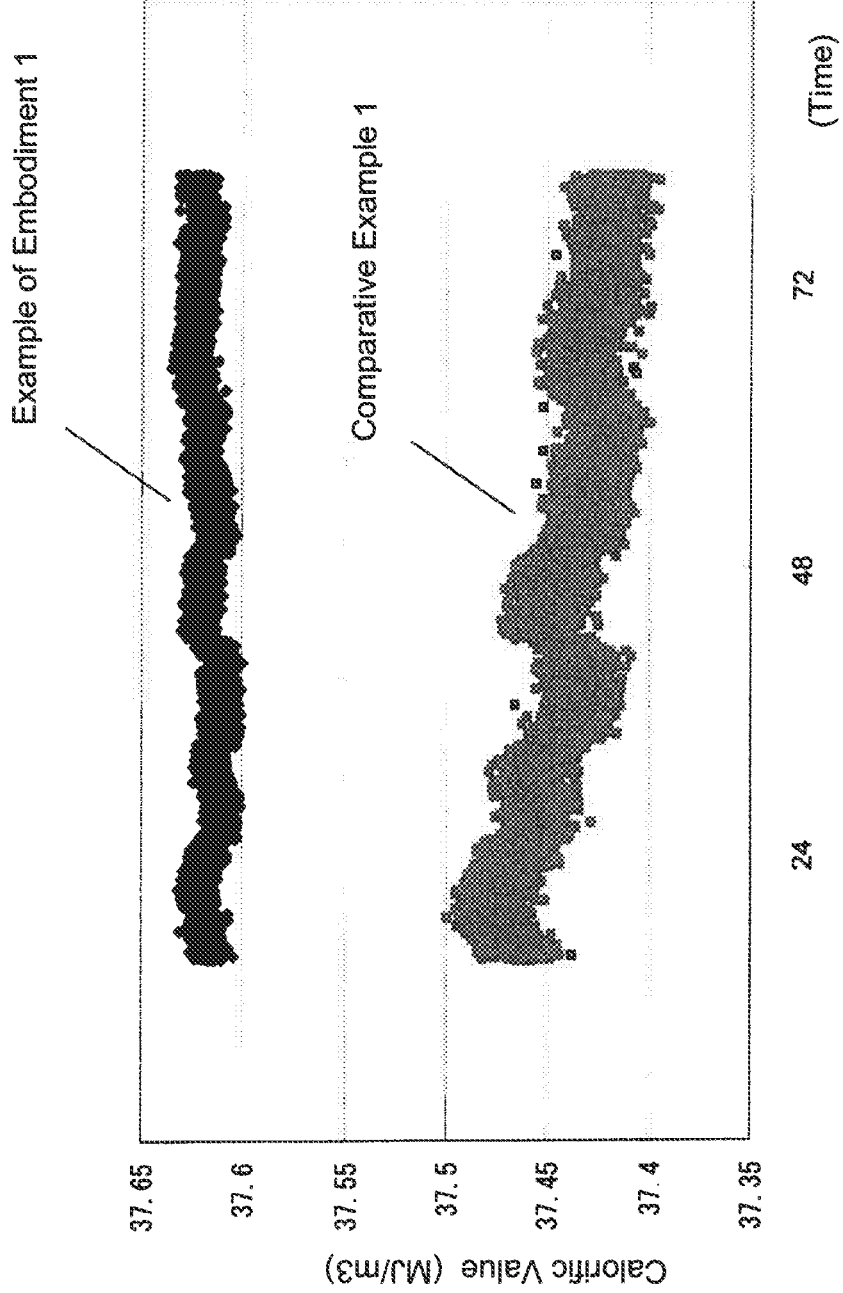
FIG. 21 is a graph showing a calculated value for the calorific value in another example according to the present invention.

In another example, the calorific value of methane gas was calculated as time elapsed using a calorific value calculating equation that does not include, as an independent variable, the electric signal $S_I$ from the temperature measuring element, generated in the above example, and a calorific value calculating equation that does include, as an independent variable, the electric signal $S_I$ from the temperature measuring element, generated in the first comparative example. The result, as shown in FIG. 21, was that when the calorific value calculating equation generated in the above example was used, the calculated calorific value for the methane gas was essentially constant, but when the calorific value calculating equation generated in the above example was used, the calculated calorific value for the methane gas went down with the passage of time.

While there are descriptions of examples as set forth above, the descriptions and drawings that form a portion of the disclosure are not to be understood to limit the present invention. A variety of alternate examples and operating technologies should be obvious to those skilled in the art. The present invention should be understood to include a variety of examples, and the like, not set forth herein.

I claim:

1. A calorific value calculating equation generating system, comprising:
   a container containing the injection of each of a plurality of mixed gases;
   a heating element, disposed in the container, producing heat at a plurality of heat producing temperatures;
   a measuring portion measuring a value of an electric signal from the heating element at a plurality of heat producing temperatures; and an equation generating portion generating a calorific value calculating equation, based on calorific values for the plurality of mixed gases and measured values for electric signals from the heating element at the plurality of heat producing temperatures, using only the electric signals from the heating element at the plurality of heat producing temperatures as independent variables and using the calorific value as the dependent variable.

2. The calorific value calculating equation generating system as set forth in claim 1, wherein:
a number of the heat producing temperatures in the plurality of heat producing temperatures of the heating element is, at least, 1 less than the number of gas components included in the respective plurality of mixed gases.

3. The calorific value calculating equation generating system as set forth in claim 1, wherein:
the equation generating portion generates the calorific value calculating equation using support vector regression.

4. The calorific value calculating equation generating system as set forth in claim 1, wherein the heating element produces heat through a supply of electric power thereto.

5. A calorific value calculating equation generating method, comprising the steps of:
preparing a plurality of mixed gases;
contacting a heating element with each of the plurality of mixed gases and producing heat at a plurality of heat producing temperatures;
measuring a value for an electric signal from the heating element at each of the plurality of heat producing temperatures; and
generating a calorific value calculating equation, based on values for calorific values for the plurality of mixed gases and measured values for electric signals from the heating element at the plurality of heat producing temperatures, using only the electric signals from the heating element at the plurality of heat producing temperatures as independent variables and using the calorific value as the dependent variable.

6. The calorific value calculating equation generating method as set forth in claim 5, wherein:
the number of heat producing temperatures in the plurality of heat producing temperatures is, at least, 1 less than the number of gas components included in the respective plurality of mixed gases.

7. The calorific value calculating equation generating method as set forth in claim 5, wherein:
using support vector regression in the generation of the calorific value calculating equation.

8. The calorific value calculating equation generating method as set forth in claim 5, wherein the heating element produces heat through a supply of electric power thereto.

9. A calorific value measuring system, comprising:
a container for an injection of a mixed gas being measured;
a heating element, disposed in the container, producing heat at a plurality of heat producing temperatures;
a measuring portion measuring a value for an electric signal from the heating element that is in contact with the mixed gas being measured at each of the plurality of heat producing temperatures;
an equation storage device storing a calorific value calculating equation that uses only electric signals from the heating element at the plurality of heat producing temperatures as independent variables and uses the calorific value as the dependent variable; and
a calorific value calculating portion calculating a value for the calorific value of the mixed gas being measured through substituting a measured value of the electric signal from the heating element into an independent variable of the calorific value calculating equation.

10. The calorific value measuring system as set forth in claim 9, wherein:
the number of heat producing temperatures in the plurality of heat producing temperatures is, at least, 1 less than the number of different types of gas components included in the mixed gas to be measured.

11. The calorific value measuring system as set forth in claim 9, wherein the heating element produces heat through a supply of electric power thereto.

12. The calorific value measuring system as set forth in claim 9, wherein:
the calorific value calculating equation was generated based on calorific values for a plurality of sample mixed gases that include a plurality of types of gas components, and respective values for electric signals from the heating element that contacts the plurality of sample mixed gases.

13. The calorific value measuring system as set forth in claim 12, wherein:
support vector regression was used in order to generate the calorific value calculating equation.

14. A calorific value measuring method, comprising the steps of:
preparing a mixed gas to be measured;
contacting a heating element with the mixed gas being measured and producing heat at a plurality of heat producing temperatures;
measuring a value for an electric signal from the heating element at each of the plurality of heat producing temperatures;
preparing a calorific value calculating equation that uses electric signals from the heating element at the plurality of heat producing temperatures as independent variables and uses the calorific value as the dependent variable; and
the calculation of a value for the calorific value of the mixed gas being measured through substituting only the measured value of the electric signal from the heating element into an independent variable of the calorific value calculating equation.

15. The calorific value measuring method as set forth in claim 14, wherein:
the number of temperatures in the plurality of temperatures is, at least, 1 less than the number of different types of gas components included in the mixed gas to be measured.

16. The calorific value measuring method as set forth in claim 14, wherein the heating element produces heat through a supply of electric power thereto.

17. The calorific value measuring method as set forth in claim 14, wherein:
the calorific value calculating equation was generated based on calorific values for a plurality of sample mixed gases that include a plurality of types of gas components, and respective values for electric signals from the heating element that contacts the plurality of sample mixed gases.

18. The calorific value measuring method as set forth in claim 17, wherein:
using support vector regression in order to generate the calorific value calculating equation.

* * * * *